United States Patent
Georgopoulos et al.

(10) Patent No.: US 11,266,719 B2
(45) Date of Patent: *Mar. 8, 2022

(54) METHODS AND COMPOSITIONS FOR TREATING MUSCLE DISEASE AND DISORDERS

(71) Applicant: PHASEBIO PHARMACEUTICALS, INC., Malvern, PA (US)

(72) Inventors: Lynne Georgopoulos, Malvern, PA (US); Susan Arnold, Malvern, PA (US); David James Ballance, Malvern, PA (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,759

(22) Filed: Jun. 22, 2020

(65) Prior Publication Data

US 2021/0069299 A1    Mar. 11, 2021

Related U.S. Application Data

(63) Continuation of application No. 15/546,037, filed as application No. PCT/US2016/017102 on Feb. 9, 2016, now Pat. No. 10,688,156.

(60) Provisional application No. 62/150,679, filed on Apr. 21, 2015, provisional application No. 62/145,770, filed on Apr. 10, 2015, provisional application No. 62/113,943, filed on Feb. 9, 2015.

(51) Int. Cl.
*A61K 38/39* (2006.01)
*A61K 38/22* (2006.01)
*A61P 9/10* (2006.01)
*A61K 9/00* (2006.01)
*A61K 47/02* (2006.01)
*A61P 9/12* (2006.01)

(52) U.S. Cl.
CPC ........ *A61K 38/2278* (2013.01); *A61K 9/0019* (2013.01); *A61K 38/39* (2013.01); *A61K 47/02* (2013.01); *A61P 9/10* (2018.01); *A61P 9/12* (2018.01)

(58) Field of Classification Search
None
See application file for complete search history.

(56) References Cited

U.S. PATENT DOCUMENTS

| | | |
|---|---|---|
| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,605,641 A | 8/1986 | Bolin et al. |
| 4,749,647 A | 6/1988 | Thomas et al. |
| 4,752,638 A | 6/1988 | Nowinski et al. |
| 4,783,523 A | 11/1988 | Urry et al. |
| 4,870,055 A | 9/1989 | Urry et al. |
| 4,898,926 A | 2/1990 | Urry |
| 5,147,855 A | 9/1992 | Gozes et al. |
| 5,234,907 A | 8/1993 | Bolin |
| 5,235,041 A | 8/1993 | Cappello et al. |
| 5,236,904 A | 8/1993 | Gerstenberg et al. |
| 5,243,038 A | 9/1993 | Ferrari et al. |
| 5,288,514 A | 2/1994 | Ellman |
| 5,376,637 A | 12/1994 | Sawai et al. |
| 5,428,015 A | 6/1995 | Kurono et al. |
| 5,445,934 A | 8/1995 | Fodor et al. |
| 5,447,912 A | 9/1995 | Gerstenberg et al. |
| 5,496,712 A | 3/1996 | Cappello et al. |
| 5,506,120 A | 4/1996 | Yamamoto et al. |
| 5,514,581 A | 5/1996 | Ferrari et al. |
| 5,519,004 A | 5/1996 | Urry |
| 5,520,672 A | 5/1996 | Urry |
| 5,527,610 A | 6/1996 | Urry |
| 5,545,617 A | 8/1996 | Dartt et al. |
| 5,624,711 A | 4/1997 | Sundberg et al. |
| 5,641,648 A | 6/1997 | Ferrari et al. |
| 5,681,816 A | 10/1997 | Korman |
| 5,702,717 A | 12/1997 | Cha et al. |
| 5,747,646 A | 5/1998 | Hakimi et al. |
| 5,770,570 A | 6/1998 | Paul et al. |
| 5,770,697 A | 6/1998 | Ferrari et al. |
| 5,773,249 A | 6/1998 | Cappello et al. |
| 5,816,259 A | 10/1998 | Rose |
| 5,830,713 A | 11/1998 | Ferrari et al. |
| 5,854,387 A | 12/1998 | Urry et al. |
| 5,900,405 A | 5/1999 | Urry |

(Continued)

FOREIGN PATENT DOCUMENTS

| | | |
|---|---|---|
| JP | 2009-525946 A | 7/2009 |
| WO | WO 1996/032406 A1 | 10/1996 |

(Continued)

OTHER PUBLICATIONS

Alcolado, et al., "VIP-dependent increase in F508del-CFTR membrane localization is mediated by PKCε." Am J Physiol Cell Physiol (2011); 301(1): C53-C65.

Ameen and Robson, "Experimental Models of Duchenne Muscular Dystrophy: Relationship with Cardiovascular Disease." Open Cardiovasc Med J. (2010); 4: 265-277.

Amruthwar and Janorkar, "Preparation and characterization of elastin-like polypeptide scaffolds for local delivery of antibiotics and proteins." J Mater Sci: Mater Med (2012); 23(12): 2903-2912.

(Continued)

*Primary Examiner* — Thomas S Heard
(74) *Attorney, Agent, or Firm* — Cooley LLP

(57) ABSTRACT

The present disclosure provides a method of treating muscle myopathy, including muscle dystrophies and cardiomyopathies, by administering stable, long-lasting vasoactive intestinal peptide therapeutic agents. These agents include one or more elastin-like peptides and can be administered at a low-dose.

15 Claims, 9 Drawing Sheets
Specification includes a Sequence Listing.

(56) References Cited

U.S. PATENT DOCUMENTS

| | | |
|---|---|---|
| 5,958,881 A | 9/1999 | Korman |
| 5,972,406 A | 10/1999 | Urry et al. |
| 5,972,883 A | 10/1999 | Gozes et al. |
| 5,998,588 A | 12/1999 | Hoffman et al. |
| 6,004,782 A | 12/1999 | Daniell et al. |
| 6,018,030 A | 1/2000 | Ferrari et al. |
| 6,037,321 A | 3/2000 | Cox et al. |
| 6,063,061 A | 5/2000 | Wallace et al. |
| 6,140,072 A | 10/2000 | Ferrari et al. |
| 6,153,655 A | 11/2000 | Martinez et al. |
| 6,184,348 B1 | 2/2001 | Ferrari et al. |
| 6,200,598 B1 | 3/2001 | Needham |
| 6,258,562 B1 | 7/2001 | Salfield et al. |
| 6,328,996 B1 | 12/2001 | Urry |
| 6,329,209 B1 | 12/2001 | Wagner et al. |
| 6,355,776 B1 | 3/2002 | Ferrari et al. |
| 6,380,154 B1 | 4/2002 | Cappello et al. |
| 6,429,188 B1 | 8/2002 | Perez et al. |
| 6,503,534 B1 | 1/2003 | Pellet et al. |
| 6,537,521 B2 | 3/2003 | Uzgiris |
| 6,541,033 B1 | 4/2003 | Shah |
| 6,582,926 B1 | 6/2003 | Chilkoti |
| 6,593,394 B1 | 7/2003 | Li et al. |
| 6,699,294 B2 | 3/2004 | Urry |
| 6,852,834 B2 | 2/2005 | Chilkoti |
| 6,998,387 B1 | 2/2006 | Goke et al. |
| 7,084,243 B2 | 8/2006 | Glaesner et al. |
| 7,094,755 B2 | 8/2006 | Burman et al. |
| 7,101,843 B2 | 9/2006 | Glaesner et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,176,278 B2 | 2/2007 | Prior |
| 7,226,910 B2 | 6/2007 | Wilson et al. |
| 7,232,879 B2 | 6/2007 | Galloway et al. |
| 7,259,233 B2 | 8/2007 | Dodd et al. |
| 7,271,149 B2 | 9/2007 | Glaesner et al. |
| 7,332,473 B2 | 2/2008 | Onoue et al. |
| 7,364,859 B2 | 4/2008 | Chilkoti |
| 7,429,458 B2 | 9/2008 | Chilkoti |
| 7,442,680 B2 | 10/2008 | Yong et al. |
| 7,459,441 B2 | 12/2008 | Minagawa et al. |
| 7,468,353 B2 | 12/2008 | Bevec |
| 7,566,691 B2 | 7/2009 | Nestor |
| 7,582,608 B2 | 9/2009 | Bokvist et al. |
| 7,709,227 B2 | 5/2010 | Dagher |
| 7,723,472 B2 | 5/2010 | Szoka |
| 7,776,815 B2 | 8/2010 | Vanderby et al. |
| 8,178,495 B2 | 5/2012 | Chilkoti |
| 8,334,257 B2 | 12/2012 | Chilkoti |
| 8,367,626 B2 | 2/2013 | Furgeson et al. |
| 8,729,018 B2 | 5/2014 | Chilkoti |
| 9,029,505 B2 | 5/2015 | Sadeghi et al. |
| 9,458,218 B2 | 10/2016 | Chilkoti |
| 9,561,262 B2 | 2/2017 | Georgopoulos et al. |
| 9,700,598 B2 | 7/2017 | Sadeghi et al. |
| 9,919,032 B2 | 3/2018 | Arnold et al. |
| 10,688,156 B2 | 6/2020 | Georgopoulos et al. |
| 2001/0034050 A1 | 10/2001 | Chilkoti |
| 2002/0045567 A1 | 4/2002 | Cappello et al. |
| 2002/0099003 A1 | 7/2002 | Wilson et al. |
| 2002/0151458 A1 | 10/2002 | Gomariz et al. |
| 2003/0059840 A1 | 3/2003 | Chilkoti |
| 2003/0059841 A1 | 3/2003 | Chilkoti |
| 2003/0158092 A1 | 8/2003 | Kai et al. |
| 2004/0063631 A1 | 4/2004 | Block |
| 2004/0110296 A1 | 6/2004 | Vargeese et al. |
| 2004/0234609 A1 | 11/2004 | Collier et al. |
| 2005/0118109 A1 | 6/2005 | Block et al. |
| 2005/0203009 A1 | 9/2005 | Pan et al. |
| 2005/0255554 A1 | 11/2005 | Chilkoti |
| 2006/0247156 A1 | 11/2006 | Vanderby et al. |
| 2007/0009602 A1 | 1/2007 | Setton et al. |
| 2007/0265197 A1 | 11/2007 | Furgeson et al. |
| 2008/0085860 A1 | 4/2008 | Bokvist et al. |
| 2008/0096811 A1 | 4/2008 | Bokvist et al. |
| 2008/0108573 A1 | 5/2008 | Duggan |
| 2008/0207492 A1 | 8/2008 | Polt et al. |
| 2008/0221041 A1 | 9/2008 | Block et al. |
| 2008/0261863 A1 | 10/2008 | Whelan et al. |
| 2008/0274961 A1 | 11/2008 | Bevec |
| 2008/0312156 A1 | 12/2008 | Setton et al. |
| 2008/0318845 A1 | 12/2008 | Bokvist et al. |
| 2008/0318865 A1 | 12/2008 | Juul-Mortensen |
| 2009/0004104 A1 | 1/2009 | Chilkoti |
| 2009/0005315 A1 | 1/2009 | Duggan |
| 2009/0092582 A1 | 4/2009 | Bogin et al. |
| 2009/0175821 A1 | 7/2009 | Bridon et al. |
| 2009/0220455 A1 | 9/2009 | Chilkoti |
| 2009/0270317 A1 | 10/2009 | Chilkoti |
| 2010/0016212 A1 | 1/2010 | Rubin et al. |
| 2010/0022455 A1 | 1/2010 | Chilkoti |
| 2010/0184651 A1 | 7/2010 | Maithal et al. |
| 2010/0256044 A1 | 10/2010 | Roth-chiarello |
| 2011/0039776 A1 | 2/2011 | Chilkoti |
| 2011/0053854 A1 | 3/2011 | Fallon et al. |
| 2011/0110916 A1 | 5/2011 | Worman et al. |
| 2011/0123487 A1 | 5/2011 | Chilkoti |
| 2011/0178017 A1 | 7/2011 | Sadeghi et al. |
| 2011/0219462 A1 | 9/2011 | Delbeck et al. |
| 2011/0236384 A1 | 9/2011 | Setton et al. |
| 2013/0065816 A1 | 3/2013 | Coy et al. |
| 2013/0079277 A1 | 3/2013 | Chilkoti |
| 2013/0085099 A1 | 4/2013 | Chilkoti |
| 2013/0116184 A1 | 5/2013 | Nichols et al. |
| 2013/0143802 A1 | 6/2013 | Chilkoti |
| 2013/0150291 A1 | 6/2013 | Jowett et al. |
| 2013/0172274 A1 | 7/2013 | Chilkoti |
| 2013/0230581 A1 | 9/2013 | Feng et al. |
| 2013/0310329 A1 | 11/2013 | Maiuri et al. |
| 2013/0310538 A1 | 11/2013 | Chilkoti |
| 2013/0315878 A1 | 11/2013 | Feng et al. |
| 2014/0024600 A1 | 1/2014 | Chilkoti et al. |
| 2014/0039053 A1 | 2/2014 | Ohnishi |
| 2014/0073667 A1 | 3/2014 | Morgan |
| 2014/0088141 A1 | 3/2014 | Binch et al. |
| 2014/0100155 A1 | 4/2014 | Madden et al. |
| 2014/0171370 A1 | 6/2014 | Arnold et al. |
| 2014/0213516 A1 | 7/2014 | Chilkoti |
| 2014/0364371 A1 | 12/2014 | Setton et al. |
| 2015/0111829 A1 | 4/2015 | Georgopoulos et al. |
| 2016/0220642 A1 | 8/2016 | Sadeghi et al. |
| 2017/0072021 A1 | 3/2017 | Georgopoulos et al. |
| 2017/0182130 A1 | 6/2017 | Arnold et al. |
| 2018/0008677 A1 | 1/2018 | Sadeghi et al. |
| 2018/0333467 A1 | 11/2018 | Georgopoulos et al. |

FOREIGN PATENT DOCUMENTS

| | | |
|---|---|---|
| WO | WO 2007/057922 A1 | 5/2007 |
| WO | WO 2007/065226 A1 | 6/2007 |
| WO | WO 2007/073486 A2 | 6/2007 |
| WO | WO 2008/030968 A2 | 3/2008 |
| WO | WO 2010/080578 A1 | 7/2010 |
| WO | WO 2011/020091 A1 | 2/2011 |
| WO | WO 2012/170524 A1 | 12/2012 |
| WO | WO 2013/177428 A2 | 11/2013 |
| WO | WO 2014/081849 A1 | 5/2014 |
| WO | WO 2014/113434 A1 | 7/2014 |
| WO | WO 2015/172046 A1 | 11/2015 |
| WO | WO 2016/081884 A2 | 5/2016 |
| WO | WO 2016/130518 A2 | 8/2016 |

OTHER PUBLICATIONS

Chappe, et al., "Vasoactive Intestinal Peptide Increases Cystic Fibrosis Transmembrane Conductance Regulator Levels in the Apical Membrane of Calu-3 Cells through a Protein Kinase C-Dependent Mechanism." The Journal of Pharmacology and Experimental Therapeutics (2008); 327(1): 226-238.

Chastre, et al., "Vasoactive intestinal peptide and its receptors in fetuses with cystic fibrosis." Am J Physiol (1989); 257(4pt1): G561-G569.

(56) References Cited

OTHER PUBLICATIONS

Choi, et al., "Synergistic airway gland mucus secretion in response to vasoactive intestinal peptide and carbachol is lost in cystic fibrosis." The Journal of Clinical Investigation (2007);, 117(10): 3118-3127.
Christensen, et al., "Predicting Transition Temperatures of Elastin-Like Polypeptide Fusion Proteins." Biomacromolecules (2013); 14(5): 1514-1519.
Delgado et al., "The significance of vasoactive intestinal peptide in immunomodulation", Pharmacological Reviews, 56(2): 249-290 (2004).
Domschke et al., "Vasoactive Intestinal Peptide in Man: Pharmacokinetics, Metabolic and Circulatory Effects," Gut, 19: 1049-1053 (1978).
Duggan, K.D. et al., "Effects of enalapril on vasoactive intestinal peptide metabolism and tissue levels", European Journal of Pharmacology, 358(1): 25-30 (1998).
Dvoráková, Magdalena Chottová. "Cardioprotective role of the VIP signaling system." Drug News Perspect (2005); 18(6): 387-391.
EP Application No. EP 10808864.1, Extended European Search Report dated Feb. 21, 2013, 6 pages.
EP Application No. EP 12796397.3, Extended European Search Report, dated Dec. 11, 2014, 9 pages.
EP Application No. EP 15789718.2, Extended European Search Report dated Oct. 27, 2017, 8 pages.
EP Application No. 16749691.8, Extended European Search Report dated Jul. 20, 2018, 17 pages.
EP Application No. 17163446.2, Extended European Search Report dated Feb. 21, 2018, 7 pages.
Free et al. "A Phase 1, Multi-center, Randomized, Double-blind, Placebo Controlled Study to Evaluate the Safety/Tolerability, Pharmacokinetic and Hemodynamic Response Following Single Ascending Subcutaneous Doses of PB 1046 (Vasomera™) in Subjects with Essential Hypertension (Trial Registry No. NCT01523067)," PhaseBio Pharmaceuticals, p. 1, Nov. 2014. Retrieved from the Internet:<http://phasebio.com/wp-content/uploads/2014/12/AHAPresentation-FINAL-V1-12NOV2014.pdf> on Aug. 7, 2015 (Aug. 7, 2015). entire document, 1 page.
Frottin et al. "The Proteomics of N-terminal Methionine Cleavage," Molecular & Cellular Proteomics 5.12 (2006) pp. 2336-2349.
Gourlet et al., "Vasoactive Intestinal Peptide (VIP) and Pituitary Adenylate Cyclase-Activating Peptide (PACAP-27, but not PACAP-38) Degradation by the Neutral Endopeptidase EC 3.4.24.11," Biochemical Pharmacology, 54: 509-515 (1997).
Hinkle, et al., "Activation of the vasoactive intestinal peptide 2 receptor modulates normal and atrophying skeletal muscle mass and force." Journal of Applied Physiology (2005); 98(2): 655-662.
Izumi et al., "Effect of Amino Terminal Methionine Residue on the Physicochemical Properties and Biological Activity of Recombinant Methionyl Human Interleukin-2 (S-6820)", Basic and Clinical Researches, vol. 24, No. 2, pp. 151-175 (and English Summary) (1990).
Kalfin et al., "Protective role of intracoronary vasoactive intestinal peptide in ischemic and reperfused myocardium." J Pharmacol Exp Ther. (1994); 268(2): 952-958.
Kobayashi et al., "Degradation of Vasoactive Intestinal Polypeptide by Rabbit Gastric Smooth Muscle Membranes," Peptides, 15(2): 323-332 (1994).
Kowalczyk, T., et al., "Elastin-like polypeptides as a promising family of genetically-engineered protein based polymers." World Journal of Microbiology and Biotechnology (2014); 30(8): 2141-2152.
Massodi, et al., "Application of Thermally Responsive Elastin-like Polypeptide Fused to a Lactoferrin-derived Peptide for Treatment of Pancreatic Cancer." Molecules (2009); 14(6): 1999-2015.
Mathioudakis, et al. "Vasoactive Intestinal Peptide Inhaled Agonists: Potential Role in Respiratory Therapeutics." Hippokratia (2013); 17(1): 12-16.
Meyer et al. "Purification of Recombinant Proteins by Fusion with Thermally-Responsive Polypeptides", Nature Biotechnology, 17:1112-1115 (1999).

Meyer et al., "Drug targeting using thermally responsive polymers and local hyperthermia," Journal of Controlled Release, 74: 213-224 (2001).
Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078.
Meyer et al., "Protein Purification by Fusion with an Environmentally Responsive Elastin-Like Polypeptide: Effect of Polypeptide Length on the Purification of Thioredoxin", Biotechnology Progress, 17: 720-728 (2001).
Meyer et al., "Targeting a Genetically Engineered Elastin-like Polypeptide to Solid Tumors by Local Hyperthermia," Cancer Res., 61(4): 1548-1554 (2001).
Miyazaki et al., "Segmental Myocardial Strain of the Left Ventricle in Patients With Duchenne Muscular Dystrophy Using Two-Dimensional Speckle Tracking Echocardiography," J. Echocardiogr., (2008) vol. 6, No. 4, pp. 100-108.
Mori et al., "Decreases in substance P and vasoactive intestinal peptide concentrations in plasma of stroke-prone spontaneously hypertensive rats." Japanese Heart Journal (1993); 34(6): 785-794.
Mow et al. "PhaseBio Pharmaceuticals Inc," pp. 1-28, Jun. 2013, entire document. Article Retrieved from the Internet:<http://phasebio.com/wp-content/uploads/2013/12/PhaseBio-Noncon-Jefferies-Presentation-2013.pdf> on Aug. 7, 2015 (Aug. 7, 2015). entire document, 28 pages.
Onoue et al., "Physicochemical and pharmacological characterization of novel vasoactive intestinal peptide derivatives with improved stability." European Journal of Pharmaceutics and Biopharmaceutics (2009); 73(1): 95-101.
Onoue et al., "Long-active analague of Vasoactive Intestinal Peptide, [R15, 20, 21, L17]-VIP-GRR (IK212532), Protects Rat Alveolar L2 Cells from the Cytotoxicity of Cigarette Smoke," Regulatory Peptides, 123:193-199 (2004).
Onyüksel et al., "A Novel Formulation of VIP in Sterically Stabilized Micelles Amplifies Vasodilation In Vivo," Pharmaceutical Research, 16(1): 155-160 (1999).
Önyüksel et al., "Human VIP-α: A long-acting, biocompatible and biodegradable peptide nanomedicine for essential hypertension," Peptides, 27: 2271-2275 (2006).
PCT/US2010/045605, International Preliminary Report on Patentability dated Feb. 14, 2012, 7 pages.
PCT/US2010/045605, International Search Report dated Jan. 5, 2011, 7 pages.
PCT/US2010/045605, Written Opinion dated Jan. 5, 2011, 6 pages.
PCT/US2012/041092, International Preliminary Report on Patentability, dated Dec. 10, 2013, 5 pages.
PCT/US2012/041092, International Search Report and Written Opinion, dated Sep. 21, 2012, 7 pages.
PCT/US2015/029926, International Preliminary Report on Patentability, dated Nov. 8, 2016, 8 pages.
PCT/US2015/029926, International Search Report and Written Opinion, dated Aug. 25, 2015, 11 pages.
PCT/US2016/017102, International Preliminary Reporton Patentability, dated Aug. 15, 2017, 14 pages.
PCT/US2016/017102, International Search Report and Written Opinion, dated Aug. 11, 2016, 19 pages.
Petkov et al., "Vasoactive intestinal peptide as a new drug for treatment of primary pulmonary hypertension." The Journal of Clinical Investigation (2003); 111(9): 1339-1346.
"PhaseBio Announces Promising Pre-clinical Results for PB1046 in Models of Duchenne Muscular Dystrophy," Apr. 22, 2015, 4 pages, XP002781492, retrieved from https://phasebio.com/phasebio-announces-promising-pre-clinicalresults-for-pb1046-in-models-of-duchenne-muscular-dystrophy/ [retrieved on May 29, 2018].
Pozo et al., "Tuning Immune Tolerance With Vasoactive Intestinal Peptide: A New Therapeutic Approach For Immune Disorders", Peptides, 28(9): 1833-1846 (2007).
Qu, et al., "Activation of CFTR Trafficking and Gating by Vasoactive Intestinal Peptide in Human Bronchial Epithelial Cells." Journal of Cellular Biochemistry (2011); 112(3): 902-908.
Rafferty, et al., "Rescue of Functional F508del Cystic Fibrosis Transmembrane Conductance Regulator by Vasoactive Intestinal

(56) References Cited

OTHER PUBLICATIONS

Peptide in the Human Nasal Epithelial Cell Line JME/CF15." Journal of Pharmacology and Experimental Therapeutics (2009); 331(1): 2-13.

Rubinstein et al., "Intratracheal and subcutaneous liposomal VIP normalizes arterial pressure in spontaneously hypertensive hamsters," International Journal of Pharmaceutics, 316: 144-147 (2006).

Said et al., "Moderate pulmonary arterial hypertension in male mice lacking the vasoactive intestinal peptide gene." Circulation (2007); 115(10): 1260-1268.

Savage, et al., "Cystic fibrosis, vasoactive intestinal polypeptide, and active cutaneous vasodilation." J Appl Physiol (1990); 69(6):2149-2154.

Sejourne et al., "Development of a Novel Bioactive Formulation of Vasoactive Intestinal Peptide in Sterically Stabilized Liposomes," Pharmaceutical Research, 14(3): 362-365 (1997).

Suzuki et al., "Encapsulation of VIP into liposomes restores vasorelaxation in hypertension in situ," Am. J. Physiol., 271(40): H282-H287 (1996).

Tan, et al., "Recent developments in liposomes, microparticles and nanoparticles for protein and peptide drug delivery." Peptides (2010); 31(1): 184-193.

Tunçel et al., "Ischemic-reperfused rat skeletal muscle: the effect of vasoactive intestinal peptide (VIP) on contractile force, oxygenation and antioxidant enzyme systems," Peptides, 1997, vol. 18, No. 2, pp. 269-275.

Unverferth et al., "Human and canine ventricular vasoactive intestinal polypeptide: decrease with heart failure." The Journal of Laboratory and Clinical Medicine (1986), 108(1): 11-16.

Uversky et al., "Structure and stability of recombinant protein depend on the extra N-terminal methionine residue: S6 permutein from direct and fusion expression systems", Biochimica et Biophysica Acta (BBA)—Protein Structure and Molecular Enzymology, 1432(2): 324-332 (1999).

Victor, Z. C., et al. "Vasopeptidase inhibition reverses myocardial vasoactive intestinal peptide depletion and decreases fibrosis in salt sensitive hypertension." European Journal of Pharmacology (2004); 485(1): 235-242.

Yang et al., "Enhanced Inhibition of Human Immunodeficiency Virus Type 1 by Met-Stromal-Derived Factor 1β Correlates with Down-Modulation of CXCR4", Journal of Virology, 73(6): 4582-4589(1999).

Ye, V. Z. C., et al. "Myocardial vasoactive intestinal peptide and fibrosis induced by nitric oxide synthase inhibition in the rat." Acta Physiologica Scandinavica (2003); 179(4): 353-360.

SEQUENCE LISTING

```
<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: ELP component sequence

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: ELP component sequence

<400> SEQUENCE: 2

Ile Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: ELP component sequence

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 5

Ile Pro Gly Xaa Gly
1               5

<210> SEQ ID NO 6
```

```
<211> LENGTH: 5
<212> TYPE: PRT
<213> ORGANISM: Artificial Sequence
<220> FEATURE:
<223> OTHER INFORMATION: ELP component sequence

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (4)..(4)
<223> OTHER INFORMATION: Xaa can be any naturally occurring or
      non-natural amino acid

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP component sequence

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP component sequence

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP component sequence

<400> SEQUENCE: 10

Gly Val Gly Val Pro Gly Val Gly
1               5

<210> SEQ ID NO 11
<211> LENGTH: 9
<212> TYPE: PRT
<213> ORGANISM: Artificial Sequence
<220> FEATURE:
<223> OTHER INFORMATION: ELP component sequence

<400> SEQUENCE: 11

Val Pro Gly Phe Gly Val Gly Ala Gly
```

-continued

<210> SEQ ID NO 12
<211> LENGTH: 9
<212> TYPE: PRT
<213> ORGANISM: Artificial Sequence
<220> FEATURE:
<223> OTHER INFORMATION: ELP component sequence

<400> SEQUENCE: 12

Val Pro Gly Val Gly Val Pro Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: ELP component sequence
<220> FEATURE:
<221> NAME/KEY: misc_feature
<222> LOCATION: (1)..(1)
<223> OTHER INFORMATION: Xaa can be any naturally occurring or
      non-natural amino acid

<400> SEQUENCE: 13

Xaa Pro Gly Val Gly
1               5

<210> SEQ ID NO 14
<211> LENGTH: 29
<212> TYPE: PRT
<213> ORGANISM: Artificial Sequence
<220> FEATURE:
<223> OTHER INFORMATION: M-VIP

<400> SEQUENCE: 14

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
            20                  25

<210> SEQ ID NO 15
<211> LENGTH: 634
<212> TYPE: PRT
<213> ORGANISM: Artificial Sequence
<220> FEATURE:
<223> OTHER INFORMATION: M-VIP ELP1-120

<400> SEQUENCE: 15

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Gly Val Pro Gly Ala
        35                  40                  45

Gly Val Pro Gly Val Gly Val Pro Gly Val Gly Val Pro Gly Val Gly
    50                  55                  60

Val Pro Gly Gly Gly Val Pro Gly Ala Gly Val Pro Gly Gly Gly Val
65                  70                  75                  80

Pro Gly Val Gly Val Pro Gly Val Gly Val Pro Gly Gly Gly Val Pro
                85                  90                  95

Gly Ala Gly Val Pro Gly Val Gly Val Pro Gly Val Gly Val Pro Gly
            100                 105                 110

```
Val Gly Val Pro Gly Gly Val Pro Gly Ala Gly Val Pro Gly Gly
            115                 120                 125
Gly Val Pro Gly Val Gly Val Pro Gly Val Gly Val Pro Gly Gly Gly
        130                 135                 140
Val Pro Gly Ala Gly Val Pro Gly Val Gly Val Pro Gly Val Gly Val
145                 150                 155                 160
Pro Gly Val Gly Val Pro Gly Gly Val Pro Gly Ala Gly Val Pro
            165                 170                 175
Gly Gly Gly Val Pro Gly Val Gly Val Pro Gly Val Gly Val Pro Gly
            180                 185                 190
Gly Gly Val Pro Gly Ala Gly Val Pro Gly Val Gly Val Pro Gly Val
        195                 200                 205
Gly Val Pro Gly Val Gly Val Pro Gly Gly Gly Val Pro Gly Ala Gly
        210                 215                 220
Val Pro Gly Gly Val Pro Gly Val Gly Val Pro Gly Val Gly Val
225                 230                 235                 240
Pro Gly Gly Gly Val Pro Gly Ala Gly Val Pro Gly Val Gly Val Pro
            245                 250                 255
Gly Val Gly Val Pro Gly Val Gly Val Pro Gly Gly Gly Val Pro Gly
        260                 265                 270
Ala Gly Val Pro Gly Gly Val Pro Gly Val Gly Val Pro Gly Val
        275                 280                 285
Gly Val Pro Gly Gly Gly Val Pro Gly Ala Gly Val Pro Gly Val Gly
        290                 295                 300
Val Pro Gly Val Gly Val Pro Gly Val Gly Val Pro Gly Gly Gly Val
305                 310                 315                 320
Pro Gly Ala Gly Val Pro Gly Gly Gly Val Pro Gly Val Gly Val Pro
            325                 330                 335
Gly Val Gly Val Pro Gly Gly Gly Val Pro Gly Ala Gly Val Pro Gly
        340                 345                 350
Val Gly Val Pro Gly Val Gly Val Pro Gly Val Gly Val Pro Gly Gly
            355                 360                 365
Gly Val Pro Gly Ala Gly Val Pro Gly Gly Gly Val Pro Gly Val Gly
        370                 375                 380
Val Pro Gly Val Gly Val Pro Gly Gly Gly Val Pro Gly Ala Gly Val
385                 390                 395                 400
Pro Gly Val Gly Val Pro Gly Val Gly Val Pro Gly Val Gly Val Pro
            405                 410                 415
Gly Gly Gly Val Pro Gly Ala Gly Val Pro Gly Gly Gly Val Pro Gly
            420                 425                 430
Val Gly Val Pro Gly Val Gly Val Pro Gly Gly Gly Val Pro Gly Ala
            435                 440                 445
Gly Val Pro Gly Val Gly Val Pro Gly Val Gly Val Pro Gly Val Gly
        450                 455                 460
Val Pro Gly Gly Gly Val Pro Gly Ala Gly Val Pro Gly Gly Gly Val
465                 470                 475                 480
Pro Gly Val Gly Val Pro Gly Val Gly Val Pro Gly Gly Gly Val Pro
            485                 490                 495
Gly Ala Gly Val Pro Gly Val Gly Val Pro Gly Val Gly Val Pro Gly
            500                 505                 510
Val Gly Val Pro Gly Gly Gly Val Pro Gly Ala Gly Val Pro Gly Gly
            515                 520                 525
```

-continued

```
Gly Val Pro Gly Val Gly Val Pro Gly Val Gly Val Pro Gly Gly Gly
            530                 535                 540
Val Pro Gly Ala Gly Val Pro Gly Val Gly Val Pro Gly Val Gly Val
545                 550                 555                 560
Pro Gly Val Gly Val Pro Gly Gly Val Pro Gly Ala Gly Val Pro
                565                 570                 575
Gly Gly Gly Val Pro Gly Val Gly Val Pro Gly Val Gly Val Pro Gly
            580                 585                 590
Gly Gly Val Pro Gly Ala Gly Val Pro Gly Val Gly Val Pro Gly Val
            595                 600                 605
Gly Val Pro Gly Val Gly Val Pro Gly Gly Val Pro Gly Ala Gly
            610                 615                 620
Val Pro Gly Gly Gly Val Pro Gly Trp Pro
625                 630

<210> SEQ ID NO 16
<211> LENGTH: 636
<212> TYPE: PRT
<213> ORGANISM: Artificial Sequence
<220> FEATURE:
<223> OTHER INFORMATION: MAA-VIP ELP1-120

<400> SEQUENCE: 16

Met Ala Ala His Ser Asp Ala Val Phe Thr Asp Asn Tyr Thr Arg Leu
1               5                   10                  15
Arg Lys Gln Met Ala Val Lys Lys Tyr Leu Asn Ser Ile Leu Asn Val
                20                  25                  30
Pro Gly Val Gly Val Pro Gly Val Gly Val Pro Gly Gly Val Pro
            35                  40                  45
Gly Ala Gly Val Pro Gly Val Gly Val Pro Gly Val Gly Val Pro Gly
50                  55                  60
Val Gly Val Pro Gly Gly Val Pro Gly Ala Gly Val Pro Gly Gly
65                  70                  75                  80
Gly Val Pro Gly Val Gly Val Pro Gly Val Gly Val Pro Gly Gly Gly
            85                  90                  95
Val Pro Gly Ala Gly Val Pro Gly Val Gly Val Pro Gly Val Gly Val
            100                 105                 110
Pro Gly Val Gly Val Pro Gly Gly Val Pro Gly Ala Gly Val Pro
            115                 120                 125
Gly Gly Gly Val Pro Gly Val Gly Val Pro Gly Val Gly Val Pro Gly
            130                 135                 140
Gly Gly Val Pro Gly Ala Gly Val Pro Gly Val Gly Val Pro Gly Val
145                 150                 155                 160
Gly Val Pro Gly Val Gly Val Pro Gly Gly Val Pro Gly Ala Gly
                165                 170                 175
Val Pro Gly Gly Gly Val Pro Gly Val Gly Val Pro Gly Val Gly Val
            180                 185                 190
Pro Gly Gly Gly Val Pro Gly Ala Gly Val Pro Gly Val Gly Val Pro
            195                 200                 205
Gly Val Gly Val Pro Gly Val Gly Val Pro Gly Gly Gly Val Pro Gly
            210                 215                 220
Ala Gly Val Pro Gly Gly Gly Val Pro Gly Val Gly Val Pro Gly Val
225                 230                 235                 240
Gly Val Pro Gly Gly Gly Val Pro Gly Ala Gly Val Pro Gly Val Gly
                245                 250                 255
```

Val Pro Gly Val Gly Val Pro Gly Val Gly Val Pro Gly Gly Val
                260                 265                 270

Pro Gly Ala Gly Val Pro Gly Gly Val Pro Gly Val Gly Val Pro
            275                 280                 285

Gly Val Gly Val Pro Gly Gly Val Pro Gly Ala Gly Val Pro Gly
        290                 295                 300

Val Gly Val Pro Gly Val Gly Val Pro Gly Val Gly Val Pro Gly Gly
305                 310                 315                 320

Gly Val Pro Gly Ala Gly Val Pro Gly Gly Val Pro Gly Val Gly
            325                 330                 335

Val Pro Gly Val Gly Val Pro Gly Gly Val Pro Gly Ala Gly Val
        340                 345                 350

Pro Gly Val Gly Val Pro Gly Val Gly Val Pro Gly Val Gly Val Pro
        355                 360                 365

Gly Gly Gly Val Pro Gly Ala Gly Val Pro Gly Gly Gly Val Pro Gly
        370                 375                 380

Val Gly Val Pro Gly Val Gly Val Pro Gly Gly Gly Val Pro Gly Ala
385                 390                 395                 400

Gly Val Pro Gly Val Gly Val Pro Gly Val Gly Val Pro Gly Val Gly
            405                 410                 415

Val Pro Gly Gly Gly Val Pro Gly Ala Gly Val Pro Gly Gly Gly Val
            420                 425                 430

Pro Gly Val Gly Val Pro Gly Val Gly Val Pro Gly Gly Gly Val Pro
            435                 440                 445

Gly Ala Gly Val Pro Gly Val Gly Val Pro Gly Val Gly Val Pro Gly
450                 455                 460

Val Gly Val Pro Gly Gly Gly Val Pro Gly Ala Gly Val Pro Gly Gly
465                 470                 475                 480

Gly Val Pro Gly Val Gly Val Pro Gly Val Gly Val Pro Gly Gly Gly
            485                 490                 495

Val Pro Gly Ala Gly Val Pro Gly Val Gly Val Pro Gly Val Gly Val
            500                 505                 510

Pro Gly Val Gly Val Pro Gly Gly Gly Val Pro Gly Ala Gly Val Pro
            515                 520                 525

Gly Gly Gly Val Pro Gly Val Gly Val Pro Gly Val Gly Val Pro Gly
        530                 535                 540

Gly Gly Val Pro Gly Ala Gly Val Pro Gly Gly Gly Val Pro Gly Val
545                 550                 555                 560

Gly Val Pro Gly Val Gly Val Pro Gly Gly Gly Val Pro Gly Ala Gly
            565                 570                 575

Val Pro Gly Gly Gly Val Pro Gly Val Gly Val Pro Gly Val Gly Val
            580                 585                 590

Pro Gly Gly Gly Val Pro Gly Ala Gly Val Pro Gly Gly Val Pro
        595                 600                 605

Gly Val Gly Val Pro Gly Val Gly Val Pro Gly Gly Gly Val Pro Gly
        610                 615                 620

Ala Gly Val Pro Gly Gly Gly Val Pro Gly Trp Pro
625                 630                 635

<210> SEQ ID NO 17
<211> LENGTH: 28
<212> TYPE: PRT
<213> ORGANISM: Homo sapiens

<400> SEQUENCE: 17

-continued

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 18
<211> LENGTH: 31
<212> TYPE: PRT
<213> ORGANISM: Artificial Sequence
<220> FEATURE:
<223> OTHER INFORMATION: MAA-VIP

<400> SEQUENCE: 18

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn
            20                  25                  30

<210> SEQ ID NO 19
<211> LENGTH: 633
<212> TYPE: PRT
<213> ORGANISM: Artificial Sequence
<220> FEATURE:
<223> OTHER INFORMATION: VIP ELP1-120

<400> SEQUENCE: 19

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Val Pro Gly Val
            20                  25                  30

Gly Val Pro Gly Val Gly Val Pro Gly Gly Gly Val Pro Gly Ala Gly
            35                  40                  45

Val Pro Gly Val Gly Val Pro Gly Val Gly Val Pro Gly Val Gly Val
        50                  55                  60

Pro Gly Gly Gly Val Pro Gly Ala Gly Val Pro Gly Gly Gly Val Pro
65                  70                  75                  80

Gly Val Gly Val Pro Gly Val Gly Val Pro Gly Gly Gly Val Pro Gly
                85                  90                  95

Ala Gly Val Pro Gly Val Gly Val Pro Gly Val Gly Val Pro Gly Val
            100                 105                 110

Gly Val Pro Gly Gly Gly Val Pro Gly Ala Gly Val Pro Gly Gly Gly
            115                 120                 125

Val Pro Gly Val Gly Val Pro Gly Val Gly Val Pro Gly Gly Gly Val
        130                 135                 140

Pro Gly Ala Gly Val Pro Gly Val Gly Val Pro Gly Val Gly Val Pro
145                 150                 155                 160

Gly Val Gly Val Pro Gly Gly Gly Val Pro Gly Ala Gly Val Pro Gly
                165                 170                 175

Gly Gly Val Pro Gly Val Gly Val Pro Gly Val Gly Val Pro Gly Gly
            180                 185                 190

Gly Val Pro Gly Ala Gly Val Pro Gly Val Gly Val Pro Gly Val Gly
            195                 200                 205

Val Pro Gly Val Gly Val Pro Gly Gly Gly Val Pro Gly Ala Gly Val
        210                 215                 220

Pro Gly Gly Gly Val Pro Gly Val Gly Val Pro Gly Val Gly Val Pro
225                 230                 235                 240

Gly Gly Gly Val Pro Gly Ala Gly Val Pro Gly Val Gly Val Pro Gly

```
                245                 250                 255
Val Gly Val Pro Gly Val Gly Val Pro Gly Gly Val Pro Gly Ala
            260                 265                 270
Gly Val Pro Gly Gly Val Pro Gly Val Gly Val Pro Gly Val Gly
            275                 280                 285
Val Pro Gly Gly Val Pro Gly Ala Gly Val Pro Gly Val Gly Val
            290                 295                 300
Pro Gly Val Gly Val Pro Gly Val Gly Val Pro Gly Gly Val Pro
305                 310                 315                 320
Gly Ala Gly Val Pro Gly Gly Val Pro Gly Val Gly Val Pro Gly
            325                 330                 335
Val Gly Val Pro Gly Gly Val Pro Gly Ala Gly Val Pro Gly Val
            340                 345                 350
Gly Val Pro Gly Val Gly Val Pro Gly Val Gly Val Pro Gly Gly
            355                 360                 365
Val Pro Gly Ala Gly Val Pro Gly Gly Val Pro Gly Val Gly Val
            370                 375                 380
Pro Gly Val Gly Val Pro Gly Gly Val Pro Gly Ala Gly Val Pro
385                 390                 395                 400
Gly Val Gly Val Pro Gly Val Gly Val Pro Gly Val Gly Val Pro Gly
            405                 410                 415
Gly Gly Val Pro Gly Ala Gly Val Pro Gly Gly Val Pro Gly Val
            420                 425                 430
Gly Val Pro Gly Val Gly Val Pro Gly Gly Val Pro Gly Ala Gly
            435                 440                 445
Val Pro Gly Val Gly Val Pro Gly Val Gly Val Pro Gly Val Gly Val
            450                 455                 460
Pro Gly Gly Gly Val Pro Gly Ala Gly Val Pro Gly Gly Val Pro
465                 470                 475                 480
Gly Val Gly Val Pro Gly Val Gly Val Pro Gly Gly Gly Val Pro Gly
            485                 490                 495
Ala Gly Val Pro Gly Val Gly Val Pro Gly Val Gly Val Pro Gly Val
            500                 505                 510
Gly Val Pro Gly Gly Val Pro Gly Ala Gly Val Pro Gly Gly Gly
            515                 520                 525
Val Pro Gly Val Gly Val Pro Gly Val Gly Val Pro Gly Gly Gly Val
            530                 535                 540
Pro Gly Ala Gly Val Pro Gly Val Gly Val Pro Gly Val Gly Val Pro
545                 550                 555                 560
Gly Val Gly Val Pro Gly Gly Val Pro Gly Ala Gly Val Pro Gly
            565                 570                 575
Gly Gly Val Pro Gly Val Gly Val Pro Gly Val Gly Val Pro Gly Gly
            580                 585                 590
Gly Val Pro Gly Ala Gly Val Pro Gly Val Gly Val Pro Gly Val Gly
            595                 600                 605
Val Pro Gly Val Gly Val Pro Gly Gly Val Pro Gly Ala Gly Val
            610                 615                 620
Pro Gly Gly Gly Val Pro Gly Trp Pro
625                 630

<210> SEQ ID NO 20
<211> LENGTH: 730
<212> TYPE: PRT
<213> ORGANISM: Artificial Sequence
```

<220> FEATURE:
<223> OTHER INFORMATION: ELPbetaV2-144

<400> SEQUENCE: 20

Val Pro Gly Val Gly Val Pro Gly Val Gly Val Pro Gly Ala Gly Val
1               5                   10                  15

Pro Gly Val Gly Val Pro Gly Ala Gly Val Pro Gly Val Gly Val Pro
            20                  25                  30

Gly Val Gly Val Pro Gly Ala Gly Val Pro Gly Val Gly Val Pro Gly
        35                  40                  45

Ala Gly Val Pro Gly Val Gly Val Pro Gly Ala Gly Val Pro Gly Val
    50                  55                  60

Gly Val Pro Gly Ala Gly Val Pro Gly Val Gly Val Pro Gly Val Gly
65                  70                  75                  80

Val Pro Gly Ala Gly Val Pro Gly Val Gly Val Pro Gly Ala Gly Val
                85                  90                  95

Pro Gly Val Gly Val Pro Gly Ala Gly Val Pro Gly Val Gly Val Pro
            100                 105                 110

Gly Ala Gly Val Pro Gly Val Gly Val Pro Gly Val Gly Val Pro Gly
        115                 120                 125

Ala Gly Val Pro Gly Val Gly Val Pro Gly Ala Gly Val Pro Gly Val
    130                 135                 140

Gly Val Pro Gly Ala Gly Val Pro Gly Val Gly Val Pro Gly Ala Gly
145                 150                 155                 160

Val Pro Gly Val Gly Val Pro Gly Val Gly Val Pro Gly Ala Gly Val
                165                 170                 175

Pro Gly Val Gly Val Pro Gly Ala Gly Val Pro Gly Val Gly Val Pro
            180                 185                 190

Gly Ala Gly Val Pro Gly Val Gly Val Pro Gly Ala Gly Val Pro Gly
        195                 200                 205

Val Gly Val Pro Gly Val Gly Val Pro Gly Ala Gly Val Pro Gly Val
    210                 215                 220

Gly Val Pro Gly Ala Gly Val Pro Gly Val Gly Val Pro Gly Ala Gly
225                 230                 235                 240

Val Pro Gly Val Gly Val Pro Gly Ala Gly Val Pro Gly Val Gly Val
                245                 250                 255

Pro Gly Val Gly Val Pro Gly Ala Gly Val Pro Gly Val Gly Val Pro
            260                 265                 270

Gly Ala Gly Val Pro Gly Val Gly Val Pro Gly Ala Gly Val Pro Gly
        275                 280                 285

Val Gly Val Pro Gly Ala Gly Val Pro Gly Val Gly Val Pro Gly Val
    290                 295                 300

Gly Val Pro Gly Ala Gly Val Pro Gly Val Gly Val Pro Gly Ala Gly
305                 310                 315                 320

Val Pro Gly Val Gly Val Pro Gly Ala Gly Val Pro Gly Val Gly Val
                325                 330                 335

Pro Gly Ala Gly Val Pro Gly Val Gly Val Pro Gly Val Gly Val Pro
            340                 345                 350

Gly Ala Gly Val Pro Gly Val Gly Val Pro Gly Ala Gly Val Pro Gly
        355                 360                 365

Val Gly Val Pro Gly Ala Gly Val Pro Gly Val Gly Val Pro Gly Ala
    370                 375                 380

Gly Val Pro Gly Val Gly Val Pro Gly Val Gly Val Pro Gly Ala Gly
385                 390                 395                 400

Val Pro Gly Val Gly Val Pro Gly Ala Gly Val Pro Gly Val
                405                 410                 415

Pro Gly Ala Gly Val Pro Gly Val Gly Val Pro Gly Ala Gly Val Pro
            420                 425                 430

Gly Val Gly Val Pro Gly Val Gly Val Pro Gly Ala Gly Val Pro Gly
        435                 440                 445

Val Gly Val Pro Gly Ala Gly Val Pro Gly Val Gly Val Pro Gly Ala
    450                 455                 460

Gly Val Pro Gly Val Gly Val Pro Gly Ala Gly Val Pro Gly Val Gly
465                 470                 475                 480

Val Pro Gly Val Gly Val Pro Gly Ala Gly Val Pro Gly Val Gly Val
                485                 490                 495

Pro Gly Ala Gly Val Pro Gly Val Gly Val Pro Gly Ala Gly Val Pro
            500                 505                 510

Gly Val Gly Val Pro Gly Ala Gly Val Pro Gly Val Gly Val Pro Gly
        515                 520                 525

Val Gly Val Pro Gly Ala Gly Val Pro Gly Val Gly Val Pro Gly Ala
    530                 535                 540

Gly Val Pro Gly Val Gly Val Pro Gly Ala Gly Val Pro Gly Val Gly
545                 550                 555                 560

Val Pro Gly Ala Gly Val Pro Gly Val Gly Val Pro Gly Val Gly Val
                565                 570                 575

Pro Gly Ala Gly Val Pro Gly Val Gly Val Pro Gly Ala Gly Val Pro
            580                 585                 590

Gly Val Gly Val Pro Gly Ala Gly Val Pro Gly Val Gly Val Pro Gly
        595                 600                 605

Ala Gly Val Pro Gly Val Gly Val Pro Gly Val Gly Val Pro Gly Ala
    610                 615                 620

Gly Val Pro Gly Val Gly Val Pro Gly Ala Gly Val Pro Gly Val Gly
625                 630                 635                 640

Val Pro Gly Ala Gly Val Pro Gly Val Gly Val Pro Gly Ala Gly Val
                645                 650                 655

Pro Gly Val Gly Val Pro Gly Val Gly Val Pro Gly Ala Gly Val Pro
            660                 665                 670

Gly Val Gly Val Pro Gly Ala Gly Val Pro Gly Val Gly Val Pro Gly
        675                 680                 685

Ala Gly Val Pro Gly Val Gly Val Pro Gly Ala Gly Val Pro Gly Val
    690                 695                 700

Gly Val Pro Gly Val Gly Val Pro Gly Ala Gly Val Pro Gly Val Gly
705                 710                 715                 720

Val Pro Gly Ala Gly Val Pro Gly Val Gly
                725                 730

<210> SEQ ID NO 21
<211> LENGTH: 605
<212> TYPE: PRT
<213> ORGANISM: artificial sequence
<220> FEATURE:
<223> OTHER INFORMATION: ELP1-120

<400> SEQUENCE: 21

Val Pro Gly Val Gly Val Pro Gly Val Gly Val Pro Gly Gly Gly Val
1               5                   10                  15

Pro Gly Ala Gly Val Pro Gly Val Gly Val Pro Gly Val Gly Val Pro
            20                  25                  30

-continued

Gly Val Gly Val Pro Gly Gly Val Pro Gly Ala Gly Val Pro Gly
            35                  40                  45
Gly Gly Val Pro Gly Val Gly Val Pro Gly Gly Val Pro Gly Gly
            50                  55                  60
Gly Val Pro Gly Ala Gly Val Pro Gly Val Gly Val Pro Gly Val
65                  70                  75                  80
Val Pro Gly Val Gly Val Pro Gly Gly Val Pro Gly Ala Gly Val
                85                  90                  95
Pro Gly Gly Gly Val Pro Gly Val Gly Val Pro Gly Val Gly Val Pro
            100                 105                 110
Gly Gly Gly Val Pro Gly Ala Gly Val Pro Gly Val Gly Val Pro Gly
            115                 120                 125
Val Gly Val Pro Gly Val Gly Val Pro Gly Gly Val Pro Gly Ala
            130                 135                 140
Gly Val Pro Gly Gly Val Pro Gly Val Gly Val Pro Gly Val Gly
145                 150                 155                 160
Val Pro Gly Gly Gly Val Pro Gly Ala Gly Val Pro Gly Gly Val
                165                 170                 175
Pro Gly Val Gly Val Pro Gly Val Gly Val Pro Gly Gly Gly Val Pro
            180                 185                 190
Gly Ala Gly Val Pro Gly Gly Val Pro Gly Val Gly Val Pro Gly
            195                 200                 205
Val Gly Val Pro Gly Gly Gly Val Pro Gly Ala Gly Val Pro Gly Val
            210                 215                 220
Gly Val Pro Gly Val Gly Val Pro Gly Gly Val Pro Gly Gly Gly
225                 230                 235                 240
Val Pro Gly Ala Gly Val Pro Gly Gly Gly Val Pro Gly Val Gly Val
                245                 250                 255
Pro Gly Val Gly Val Pro Gly Gly Gly Val Pro Gly Ala Gly Val Pro
            260                 265                 270
Gly Val Gly Val Pro Gly Val Gly Val Pro Gly Gly Val Pro Gly
            275                 280                 285
Gly Gly Val Pro Gly Ala Gly Val Pro Gly Gly Gly Val Pro Gly Val
            290                 295                 300
Gly Val Pro Gly Val Gly Val Pro Gly Gly Gly Val Pro Gly Ala Gly
305                 310                 315                 320
Val Pro Gly Val Gly Val Pro Gly Val Gly Val Pro Gly Gly Val
                325                 330                 335
Pro Gly Gly Gly Val Pro Gly Ala Gly Val Pro Gly Gly Gly Val Pro
            340                 345                 350
Gly Val Gly Val Pro Gly Val Gly Val Pro Gly Gly Gly Val Pro Gly
            355                 360                 365
Ala Gly Val Pro Gly Val Gly Val Pro Gly Val Gly Val Pro Gly Val
            370                 375                 380
Gly Val Pro Gly Gly Gly Val Pro Gly Ala Gly Val Pro Gly Gly Gly
385                 390                 395                 400
Val Pro Gly Val Gly Val Pro Gly Val Gly Val Pro Gly Gly Gly Val
                405                 410                 415
Pro Gly Ala Gly Val Pro Gly Val Gly Val Pro Gly Val Gly Val Pro
            420                 425                 430
Gly Val Gly Val Pro Gly Gly Gly Val Pro Gly Ala Gly Val Pro Gly
            435                 440                 445

```
Gly Gly Val Pro Gly Val Gly Val Pro Gly Val Gly Val Pro Gly Gly
    450                 455                 460

Gly Val Pro Gly Ala Gly Val Pro Gly Val Gly Val Pro Gly Val Gly
465                 470                 475                 480

Val Pro Gly Val Gly Val Pro Gly Gly Gly Val Pro Gly Ala Gly Val
                485                 490                 495

Pro Gly Gly Gly Val Pro Gly Val Gly Val Pro Gly Val Gly Val Pro
            500                 505                 510

Gly Gly Gly Val Pro Gly Ala Gly Val Pro Gly Val Gly Val Pro Gly
        515                 520                 525

Val Gly Val Pro Gly Val Gly Val Pro Gly Gly Gly Val Pro Gly Ala
    530                 535                 540

Gly Val Pro Gly Gly Gly Val Pro Gly Val Gly Val Pro Gly Val Gly
545                 550                 555                 560

Val Pro Gly Gly Gly Val Pro Gly Ala Gly Val Pro Gly Val Gly Val
                565                 570                 575

Pro Gly Val Gly Val Pro Gly Val Gly Val Pro Gly Gly Gly Val Pro
            580                 585                 590

Gly Ala Gly Val Pro Gly Gly Gly Val Pro Gly Trp Pro
        595                 600                 605
```

METHODS AND COMPOSITIONS FOR TREATING MUSCLE DISEASE AND DISORDERS

CROSS-REFERENCE TO RELATED APPLICATIONS

This Application is a continuation of U.S. Utility application Ser. No. 15/546,037, filed Jul. 25, 2017, which is a U.S. National Phase of PCT/US2016/017102, filed Feb. 9, 2016, and claims the benefit of U.S. Provisional Application No. 62/113,943 filed Feb. 9, 2015, U.S. Provisional Application No. 62/145,770 filed Apr. 10, 2015, and 62/150,679, filed Apr. 21, 2015, the contents of each of which are hereby incorporated by reference in their entireties.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: PHAS_032_05US_SeqList_ST25.txt, date recorded: Jun. 22, 2020, file size 32 kilobytes).

BACKGROUND

Duchenne and Becker muscular dystrophies (DMD and BMD) represent the most frequent neuromuscular diseases in human, occurring in one of 3,500 to one in 6,000 live male births depending on the population studied (Bushby et al. (2010)). DMD and BMD are allelic disorders resulting from mutations in the dystrophin gene. In DMD, functioning dystrophin is completely absent from muscle, while in BMD there is some dystrophin present, although not in sufficient amounts for normal muscle function. In addition to skeletal muscle weakness, dystrophin deficiency in the myocardium results in a progressive cardiomyopathy.

Currently there are no approved therapies specific to the treatment of DMD/BMD. High dose corticosteroids are often used to treat muscle weakness and to maintain ambulation as long as possible, but these are associated with unacceptable side effects and/or suboptimal responses. It is also uncertain whether these therapeutics help or hinder cardiac function. Additional therapeutic approaches are needed to treat both the skeletal and cardiac abnormalities of muscular dystrophies.

SUMMARY OF THE INVENTION

The present disclosure provides long-lasting Vasoactive Intestinal Peptide (VIP) therapeutics to treat, delay, prevent, or ameliorate muscle myopathy. Myopathic muscles sustain damage during repeated contractions but, because they lack the ability to properly repair themselves, the muscles develop defects such as fibrotic lesions. These defects can inhibit muscle function, often by impairing the muscle's ability to contract. Preventing, delaying, or ameliorating these defects from forming can treat muscle myopathy in patients. The VIP therapeutics disclosed herein can also improve cardiac function in patients with muscle myopathies.

In some aspects, the present disclosure provides a method for treating muscle myopathy comprising administering to a patient in need thereof a pharmaceutical composition comprising a Vasoactive Intestinal Peptide (VIP) and one or more elastin-like peptides (ELP).

In some aspects, the present disclosure provides a method for protecting against muscle contraction-induced injury in a patient in need thereof comprising administering a pharmaceutical composition comprising a Vasoactive Intestinal Peptide (VIP) and one or more elastin-like peptides (ELP).

In some aspects, the present disclosure provides a method for slowing the progression of cardiomyopathy comprising administering to a patient in need thereof a pharmaceutical composition comprising a Vasoactive Intestinal Peptide (VIP) and one or more elastin-like peptides (ELP).

In some aspects, the present disclosure provides a method for treating cardiomyopathy comprising administering to a patient in need thereof a pharmaceutical composition comprising a Vasoactive Intestinal Peptide (VIP) and one or more elastin-like peptides (ELP).

In some aspects, the pharmaceutical composition comprises the amino acid sequence of SEQ ID NO: 15.

DETAILED DESCRIPTION

Figure 1A:
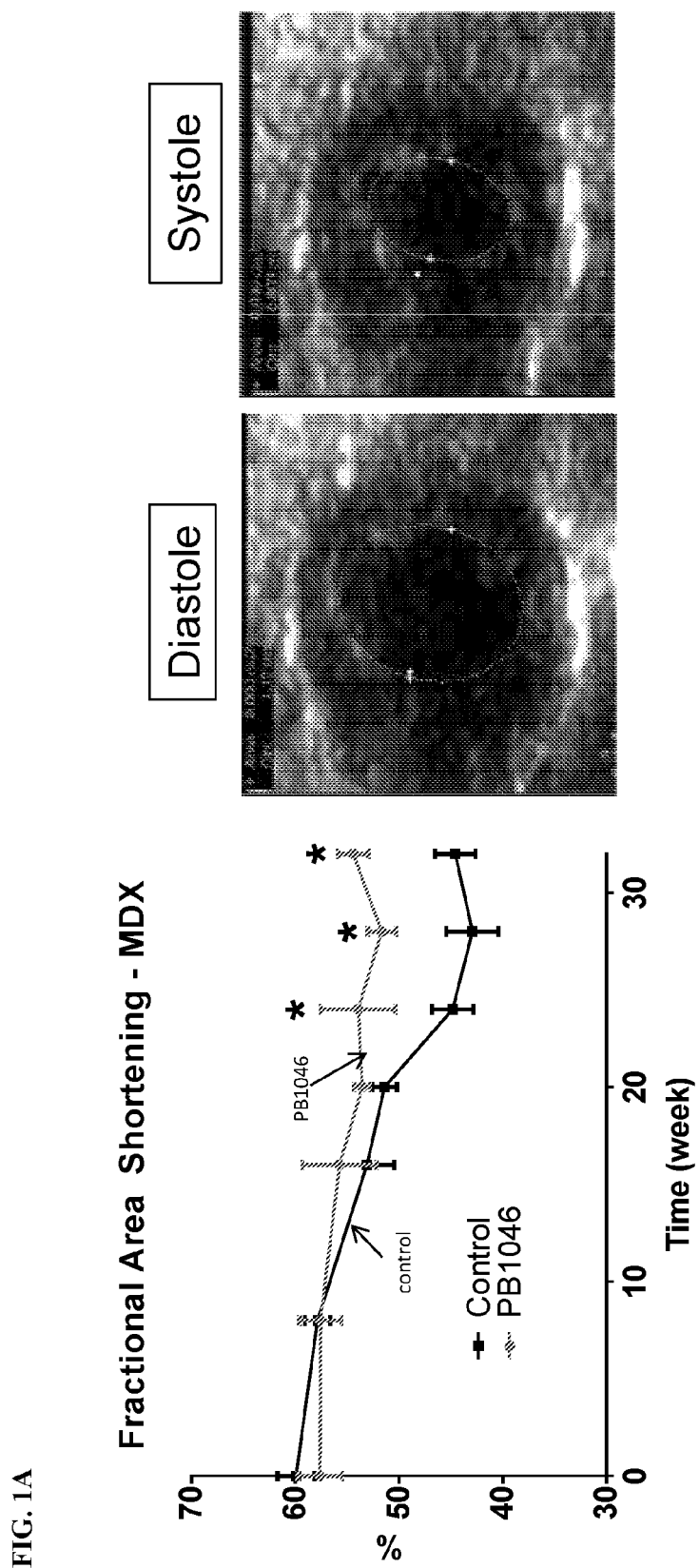
FIG. 1A-B shows cardiac function monitored via echocardiography: n=10-11, *P<0.05 vs controls. Panel A shows the fractional area shortening in MDX (dystrophin deficient mice). Panel B shows the E/A ratio in MDX mice. PB1046 treatment preserves fractional area shortening after 32 weeks of treatment PB1046 administration before cardiomyopathy developed preserved the QRS duration in mdx and double knockout mice, and slowed the deterioration of cardiac function (fractional area shortening and E/A ratios) in mdx mice.

Muscle myopathies, which may affect skeletal or cardiac muscle, are disorders in which muscle fibers no longer function correctly, resulting in muscle weakness which can lead to muscle wasting, paralysis, and even death. Cardiac dysfunction is a frequent manifestation of various muscular myopathies, and is a common cause of death for individuals with these conditions.

Often, in inherited myopathies such as muscular dystrophies, patients exhibit a mutation in the dystrophin gene. The dystrophin gene plays both a structural and regulatory role in muscle contraction. Dystrophin is part of a larger membrane-spanning complex, the dystrophin glycoprotein complex (DGC) (Lapidos et al. (2004)), the absence of which directly impacts contractility. In many muscular myopathy patients (e.g. Duchenne or Becker Muscular Dystrophies, or dystrophin-associated cardiomyopathy), the dystrophin protein may be completely absent or only partially functioning.

Absence of dystrophin increases intracellular calcium and results in an overproduction of nitric oxide, which triggers protein degradation, fibrosis, necrosis, the activation of macrophages, and ultimately results in skeletal and cardiomyopathy (Townsend et al. (2011); Judge et al (2011)).

In cardiomyocytes, these pathologic consequences are mediated in part by an increase in calcium permeability and increased myocyte calcium concentrations, which in turn initiates a cascade of events including expression of inflammatory cytokines within the myocytes, and inflammatory cells responding to myocyte necrosis (Zhou et al (2010); Klinger et al. (2012)). Further, disruption of intracellular cyclic guanosine monophosphate (cGMP) signaling pathways directly contributes to loss of muscle function (Lapidos et al (2004)); Townsend et al. (2011); Byers et al. (1991)).

In addition to direct effects on muscle function, the loss of dystrophin and consequent changes in nitric oxide synthase activity results in mitochondrial and metabolic stress which stimulates cytokine production and cell apoptosis. These events result in further loss of muscle mass, loss of muscle function, and ultimately in fibrosis. In particular, cardiomyocyte stress increases production of IL-6 and TGF-β, which stimulate fibroblasts, collagen synthesis, and infiltration of macrophages, all of which contribute to the increased fibrosis.

In healthy muscles, following acute tissue injury, infiltrating inflammatory cells and resident stem cells restore tissue homeostasis. However, during chronic tissue damage, such as in muscular dystrophies, inflammatory-cell infiltration and fibroblast activation persist, while the reparative capacity of stem cells (e.g. satellite cells) is attenuated. In many dystrophies the muscle undergoes constant cycles of fiber degeneration associated with chronic inflammation. In DMD, the satellite-cell population responsible for repairing muscle damage is either exhausted over time, or it loses the capacity to mediate repair, and the muscle tissue is progressively replaced by adipose and fibrotic tissue. Fibrosis and loss of muscle tissue in dystrophies reduces motile and contractile functions.

Muscular fibrosis is the excessive formation of fibrous bands of scar tissue in between muscle fibers. Although fibrosis may develop in any organ, skeletal muscle fibrosis and cardiac muscle fibrosis are the only known muscle fibroses. Fibrous scar tissue develops after the muscle has been damaged to fill in the open spaces in the injured muscle, providing more surface area for the regenerating muscle fibers to adhere to. The connective tissue cells that comprise scar tissue are unable to contract and relax to enable movement. Once the overproduction of fibrous scar tissue begins, the muscle becomes progressively weaker.

Vasoactive Intestinal Peptide (VIP) plays a role in the development of fibrosis. VIP acts through the VPAC1 and VPAC2 receptors to, among other activities, increase cAMP and cGMP levels. Importantly, in murine macrophages, VIP has been shown to decrease TGF-β production, an important mediator of cardiac fibrosis in DMD (Ameen et al. (2010); Burks et al. (2011); Bujak et al. (2007)). VIP also stimulates regulatory T cells ($T_{reg}$) which suppress muscle inflammation and injury in muscular dystrophy (Villata et al. (2014)).

The present disclosure provides a method of preventing, delaying, or ameliorating the onset of symptoms (including the development of muscle fibrosis) in myopathy patients by administering stable, long-acting Vasoactive Intestinal Peptide (VIP) therapeutics.

Vasoactive Intestinal Peptides

Vasoactive intestinal peptide (VIP) is a neuropeptide which binds to two receptors, VPAC1 and VPAC2. VIP and its functionally and structurally related analogs are known to have many physiological functions, including smooth muscle relaxation (bronchodilation, intestinal mobility) and modulation of various immune functions (anti-inflammation, immune cell protection) (Hinkle et al. (2005)).

Mature VIP has 28 amino acid residues with the following sequence: HSDAVFTDNYTRLRKQMAVKKYLNSILN (SEQ ID NO: 17). VIP results from processing of the 170-amino acid precursor molecule prepro-VIP. Structures of VIP and exemplary analogs have been described in U.S. Pat. Nos. 4,835,252, 4,939,224, 5,141,924, 4,734,400, 4,605,641, 6,080,837, 6,316,593, 5,677,419, 5,972,883, 6,489,297, 7,094,755, and 6,608,174.

In some aspects the disclosure provides therapeutic compositions that may include one or more VIP peptides, variants, or analogs. In some embodiments, the VIP peptide is a variant. In some embodiments, the VIP peptide is an analog. In some embodiments, the VIP peptide is mature VIP (e.g. SEQ ID NO: 17). In some embodiments, the VIP peptide is modified compared to mature VIP (e.g. SEQ ID NO: 17). In some embodiments, the modified VIP peptide is a variant compared to mature VIP (e.g. SEQ ID NO: 17). In some embodiments, the modified VIP peptide is a functional variant compared to mature VIP (e.g. SEQ ID NO: 17). In some embodiments, the modified VIP peptide is a functional analog compared to mature VIP (e.g. SEQ ID NO: 17).

In some embodiments, the modified VIP peptide contains one or more amino acid substitutions compared to the amino acid sequence of mature VIP (e.g. SEQ ID NO: 17). In some embodiments, one to 20 amino acids are substituted compared to the amino acid sequence of mature VIP (SEQ ID NO: 17). In some embodiments, the modified VIP peptide contains about 1, about 2, about 3. about 4, about 5, about 6, about 7, about 8, about 9, or about 10 amino acid substitutions compared to the amino acid sequence of mature VIP (SEQ ID NO: 17).

In some embodiments, the modified VIP peptide contains one or more amino acid deletions compared to the amino acid sequence of mature VIP (SEQ ID NO: 17). In some embodiments, one to 20 amino acids are deleted compared to the amino acid sequence of mature VIP (SEQ ID NO: 17). In some embodiments, the modified VIP peptide has about 1, about 2, about 3, about 4, about 5, about 6, about 7, about 8, about 9, or about 10 amino acid deletions compared to the amino acid sequence of mature VIP (SEQ ID NO: 17). In some embodiments, one to ten amino acids are deleted at either terminus compared to the amino acid sequence of mature VIP (SEQ ID NO: 17). In some embodiments, one to ten amino acids are deleted from both termini compared to the amino acid sequence of mature VIP (SEQ ID NO: 17). In some embodiments, the amino acid sequence of the modified VIP peptide is at least about 70% identical to the amino acid sequence of mature VIP (SEQ ID NO: 17). In some embodiments, the amino acid sequence of the modified VIP peptide is about 70%, about 80%, about 85%, about 90%, about 95%, about 96%, or about 97% identical to the amino acid sequence of mature VIP (SEQ ID NO: 17). Percentage identity can be calculated using the alignment program ClustalW2, available at http://www.ebi.ac.uk/Tools/psa/emboss_needle/. The following default parameters may be used for Pairwise alignment: Protein Weight Matrix=BLOSUM62; Gap Open=10; Gap Extension=0.1.

In various aspects, the present disclosure provides a modified VIP peptide having relative receptor preference for VPAC2 or VPAC1, as compared to mature VIP (i.e., SEQ ID NO: 17). For example, the modified VIP peptide may have a relative binding preference for VPAC2 over VPAC1 of at least about 2:1, about 5:1, about 10:1, about 25:1, about 50:1, about 100:1, about 500:1 or more. In other embodiments, the modified VIP peptide may have a relative binding preference for VPAC1 over VPAC2 of at least about 2:1, about 5:1, about 10:1, about 25:1, about 50:1, about 100.1, about 500:1, or more. For example, in certain embodiments, the modified VIP peptide activates the VPAC2 receptor with an EC50 within a factor of about 2-4 of mature human VIP (SEQ ID NO: 17) However, in some embodiments, this same modified VIP peptide is 50- or 100-fold or more less potent than mature, unmodified, human VIP peptide (SEQ ID NO: 17) in activating the VPAC1 receptor.

In some embodiments, the modified VIP peptide contains additional amino acid residues compared to mature VIP (SEQ ID NO: 17). In some embodiments, the modified VIP peptide contains an one or more amino acids added at the N- and/or C-terminus compared to mature VIP (SEQ ID NO: 17). Such modified VIP peptides may contain modified N-terminal regions, such as an addition of from 1 to about 500 amino acids to the N-terminal histidine of VIP, which may include heterologous mammalian (e.g. non-human) amino acid sequences. The additional sequence added to the N-terminus of VIP may be of any sequence, including biologically active and biologically inert sequences of from 1 to about 100, 1 to about 50, 1 to about 20, 1 to about 10, and 1 to about 5 amino acids. For example, the modified VIP may contain a single methionine at the N-terminal end of the natural N-terminal histidine of mature VIP. While methionine can sometimes be removed by methionine aminopeptidase (MA) in bacterial expression systems, histidine (H) is one of the least favored residues at position 2 for MA. In some embodiments, the modified VIP peptide is SEQ ID NO: 14. Such modified VIP peptides containing an N-terminal methionine can be prepared in *E. coli* or other bacterial or yeast expression systems, since the methionine will not be removed by *E. coli* when the adjacent amino acid is histidine. Alternatively, the N-terminal amino acid may be any of the naturally-occurring amino acids, namely alanine, arginine, asparagine, aspartic acid, cysteine, glutamic acid, glutamine, glycine, histidine, isoleucine, leucine, lysine, methionine, phenylalanine, serine, threonine, tryptophan, tyrosine, valine, and proline. In other embodiments, the VIP peptide is activatable by a peptidase or protease, such as an endogenous peptidase or protease. Such activatable sequences are described, for example, in International Application No. PCT/US2009/068656. As used herein, the terms "peptidase" and "protease" are interchangeable. For example, the VIP peptide may be designed to be activatable by a dipeptidyl peptidase. Exemplary dipeptidyl peptidases include dipeptidyl peptidase-1 (DPP-I), dipeptidyl peptidase-3 (DPP-III), dipeptidyl peptidase-4 (DPP-IV), dipeptidyl peptidase-6 (DPP-VI), dipeptidyl peptidase-7 (DPP-VII), dipeptidyl peptidase-8 (DPP-VIII), dipeptidyl peptidase-9 (DPP-IX), dipeptidyl peptidase-10 (DPP-X). Substrate sequences for such dipeptidases are known.

In some embodiments, the N-terminus of an activatable VIP peptide may have the structure Z—N, where Z is a substrate for a dipeptidase (e.g., Z is removed by dipeptidase exposure), and N is the N-terminus of VIP. The activatable VIP peptide may have an N-terminal sequence with the formula M-X—N where M is methionine, X is Pro, Ala, or Ser, and N is the N-terminal of VIP or VIP analog. In this manner, M and X will be sensitive to, and removed by a host cell (e.g., *E. coli*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is the N-terminal of VIP. X1-X2 is a substrate for dipeptidase (e.g., DPP-IV), and dipeptidase digestion will expose N, the desired N-terminus of the VIP or the VIP analog. In such embodiments, the VIP peptide may be produced by expression of a construct encoding M-X1-X2-N (where M is methionine) in a host cell (e.g., *E. coli*.), since Gly, Ala, Ser, Cys, Thr, Val, or Pro at the second position will signal the removal of the Met, thereby leaving X1-X2 on the N-terminus, which can be activated by a dipeptidase (e.g., DPP-IV) in vivo. In some embodiments, the peptidase may be present in the body and act on the activatable VIP peptide after injection. In some embodiments, the activatable VIP peptide contains the amino acid sequence MAA added at the N-terminus compared to mature VIP (e.g. SEQ ID NO: 17). In some embodiments, the activatable VIP peptide is SEQ ID NO: 18.

In other embodiments, the N-terminus of the modified activatable VIP peptide has the structure M-Z—N, where M is methionine, Z is a substrate for a dipeptidase (e.g., Z is removed by dipeptidase exposure), and N is a non-His N-terminal of an activatable VIP. For example, the modified activatable VIP peptide may have an N-terminal sequence with the formula M-X—N where M is methionine; X is Pro, Ala, or Ser; and N is a non-His N-terminal of the activatable VIP. In this manner, M and X will be sensitive to, and removed by a host cell (e.g., *E. coli*.), and/or a dipeptidase (e.g., DPP-IV), subsequently. Alternatively, the N-terminal sequence of the activatable VIP peptide may be X1-X2-N, where X1 is Gly, Ala, Ser, Cys, Thr, Val, or Pro; X2 is Pro, Ala, or Ser; and N is a non-His N-terminal of the activatable VIP. X1-X2 is a substrate for dipeptidase (e.g., DPP-IV), and dipeptidase digestion will expose N, the desired non-His N-terminus of the VIP.

Still other embodiments, the N-terminus of an activatable VIP peptide has the structure M-Z—S—N, where M is methionine; Z is a substrate for a dipeptidase (e.g., Z is removed by dipeptidase exposure); N is the N-terminus of mature VIP (His); and S is one or more amino acids which will be exposed after dipeptidase digestion, and which provide an activatable VIP as previously described. For example, the activatable VIP peptide may have an N-terminal sequence with the formula M-X—S—N where M is methionine, X is Pro, Ala, or Ser; N is the N-terminal of mature VIP (e.g. SEQ ID NO: 17); and S is one or more amino acids which will be exposed after dipeptidase digestion, and will provide receptor preference. Alternatively, the N-terminal sequence of the activatable VIP peptide may be X1-X2-S—N, where X1 is Gly, Ala, Ser, Cys, Thr, Val, or Pro; X2 is Pro, Ala, or Ser; N is a non-His N-terminal of VIP; and S is one or more amino acids which will be exposed after dipeptidase digestion. X1-X2 is a substrate for dipeptidase (e.g., DPP-IV), and dipeptidase digestion will expose S.

In still other embodiments, the VIP peptide is modified by fusion with a mammalian heterologous protein, such as a mammalian protein effective for extending half-life of therapeutic molecules. Such sequences may be mammalian sequences. such as albumin, transferrin, or antibody Fc sequences. Such sequences are described in U.S. Pat. No. 7,238,667 (particularly with respect to albumin fusions), U.S. Pat. No. 7,176,278 (particularly with respect to transferrin fusions), and U.S. Pat. No. 5,766,883. In some embodiments, the VIP peptide is modified by fusion with a mammalian heterologous protein at the N-terminus. In some embodiments, the VIP is modified by fusion with a mammalian heterologous protein at the C-terminus. In some embodiments, the VIP is modified by fusion with a mammalian heterologous protein at both the N- and C-termini.

In some embodiments, N-terminal chemical modifications to the VIP peptide N-terminus provides receptor preference. Chemical modification of proteins and methods thereof are well known in the art. Non-limiting exemplary chemical modifications are PEGylation, methylglyoxalation, reductive alkylation, performic acid oxidation, succinylation, aminoethylation, and lipidation (Clifton, New Protein Techniques, New Jersey: Humana Press, 1985. ISBX. 0-89603-126-8. Volume. 3 of. Methods in Molecular Biology). Chemical groups, such as PEGylation, may be attached by modifications of cysteine, methionine, histidine, lysine, arginine, tryptophan, tyrosine, carboxyl groups have been described previously (see Lundblad, Techniques in Protein Modification, CRC Press, 1995).

In still other embodiments, the VIP peptide is modified by fusion with a protein including a repeating amino acid sequence, such as a sequence comprising prolines, alanines, and serines (e.g. PASylation (Schlapschy, M. et al. (2013)), or XTEN sequences (Schellenberger, V. et al. (2009)).

Elastin-Like Peptides

In some aspects the disclosure provides therapeutic compositions that include a Vasoactive Intestinal Peptide and one or more elastin-like peptides (ELP). In some embodiments, a VIP peptide and one or more ELPs are fused together. In some embodiments, a VIP peptide and one or more ELPs are produced as a recombinant fusion polypeptide. In some embodiments, the therapeutic composition includes a Vasoactive Intestinal Peptide and one or more ELPs as separate molecules. In yet other embodiments, the compositions include a VIP-ELP fusion protein and ELPs as separate molecules. In some embodiments, the compositions include SEQ ID NO. 15. In some embodiments, the compositions include SEQ ID NO: 19. In some embodiments, the compositions include SEQ ID NO: 16.

The ELP sequence includes structural peptide units or sequences that are related to, or mimics of, the elastin protein. The ELP sequence is constructed from structural units of from three to about twenty amino acids, or in some embodiments, from four to ten amino acids, such as four, five or six amino acids. The length of the individual structural units may vary or may be uniform. For example, structural units include units defined by SEQ ID NOS: 1-13, which may be employed as repeating structural units, including tandem-repeating units, or may be employed in some combination. Thus, the ELP includes essentially structural unit(s) selected from SEQ ID NOS: 1-13.

In some embodiments, the amino acid sequence of the ELP unit is from about 1 to about 500 structural units, or in certain embodiments about 9 to about 200 structural units, or in certain embodiments about 10 to 200 structural units, or in certain embodiments about 50 to about 200 structural units, or in certain embodiments from about 80 to about 200 structural units, or from about 80 to about 150 structural units, such as one or a combination of units defined by SEQ ID NOS. 1-13. Thus, the structural units collectively may have a length of from about 50 to about 2000 amino acid residues, or from about 100 to about 800 amino acid residues, or from about 200 to about 700 amino acid residues, or from about 400 to about 600 amino acid residues. In exemplary embodiments, the amino acid sequence of the ELP structural unit includes about 3 structural units, about 7 structural units, about 9 structural units, about 10 structural units, about 15 structural units, about 20 structural units, about 40 structural units, about 80 structural units, about 90 structural units, about 100 structural units, about 120 structural units, about 140 structural units, about 144 structural units, about 160 structural units, about 180 structural units, about 200 structural units, or about 500 structural units. In exemplary embodiments, the structural units collectively have a length of about 45 amino acid residues, of about 90 amino acid residues, of about 100 amino acid residues, of about 200 amino acid residues, of about 300 amino acid residues, of about 400 amino acid residues, of about 500 amino acid residues, of about 600 amino acid residues, of about 700 amino acid residues, of about 720 amino acid residues, of about 800 amino acid residues, or of about 1000 amino acid residues.

The ELP amino acid sequence may exhibit a visible and reversible inverse phase transition with the selected formulation. That is, the ELP amino acid sequence may be structurally disordered and highly soluble in the formulation below a transition temperature (Tt), but exhibit a sharp (2-3° C. range) disorder-to-order phase transition when the temperature of the formulation is raised above the Tt. In addition to temperature, length of the amino acid polymer, amino acid composition, ionic strength, pH, pressure, temperature, selected solvents, presence of organic solutes, and protein concentration may also affect the transition properties, and these may be tailored in the formulation for the desired absorption profile. The absorption profile can be easily tested by determining plasma concentration or activity of the active agent over time.

In certain embodiments, the ELP component(s) may be formed of multipeptide structural units (e.g. tetrapeptides, pentapeptides, hexapeptides, octapeptides, or nonapeptides), including but not limited to:

(a) the tetrapeptide Val-Pro-Gly-Gly, or VPGG (SEQ ID NO: 1);

(b) the tetrapeptide Ile-Pro-Gly-Gly, or IPGG (SEQ ID NO. 2), (c) the pentapeptide Val-Pro-Gly-X-Gly (SEQ ID NO: 3), or VPGXG, where X is any natural or non-natural amino acid residue, and where X optionally varies among polymeric or oligomeric repeats;

(d) the pentapeptide Ala-Val-Gly-Val-Pro, or AVGVP (SEQ ID NO: 4);

(e) the pentapeptide Ile-Pro-Gly-X-Gly, or IPGXG (SEQ ID NO: 5), where X is any natural or non-natural amino acid residue, and where X optionally varies among polymeric or oligomeric repeats;

(e) the pentapeptide Ile-Pro-Gly-Val-Gly, or IPGVG (SEQ ID NO: 6);

(f) the pentapeptide Leu-Pro-Gly-X-Gly, or LPGXG (SEQ ID NO: 7), where X is any natural or non-natural amino acid residue, and where X optionally varies among polymeric or oligomeric repeats;

(g) the pentapeptide Leu-Pro-Gly-Val-Gly, or LPGVG (SEQ ID NO: 8);

(h) the hexapeptide Val-Ala-Pro-Gly-Val-Gly, or VAPGVG (SEQ ID NO: 9);

(i) the octapeptide Gly-Val-Gly-Val-Pro-Gly-Val-Gly, or GVGVPGVG (SEQ ID NO: 10);

(j) the nonapeptide Val-Pro-Gly-Phe-Gly-Val-Gly-Ala-Gly, or VPGFGVGAG (SEQ ID NO: 11);

(k) the nonapeptides Val-Pro-Gly-Val-Gly-Val-Pro-Gly-Gly, or VPGVGVPGG (SEQ ID NO: 12); and (l) the pentapeptide Xaa-Pro-Gly-Val-Gly, or XPGVG (SEQ ID NO:13) where X is any natural or non-natural amino acid residue, and where X optionally varies among polymeric or oligomeric repeats.

The multipeptide structural units as defined in SEQ ID NOs: 1-13 form the elastin-like peptide component, or may be used in combination to form an ELP. In some embodiments, the ELP includes more than one structural unit. In some embodiments, the ELP includes two or more structural units of any of SEQ ID NOs: 1-13, which may be in any combination. In some embodiments, the two or more structural units are the same and are repeated tandemly. In some embodiments, the two or more structural units are different and are repeated alternately. In some embodiments, the ELP includes structural units repeated tandemly for one or more portions of sequence, and also different structural units repeated alternately for other portions of the sequence. In some embodiments, the ELP component is formed entirely (or almost entirely) of one or a combination of (e.g., 2, 3 or 4) structural units selected from SEQ ID NOS: 1-13 In other embodiments, at least 75%, or at least 80%, or at least 90% of the ELP component is formed from one or a combination of structural units selected from SEQ ID NOS: 1-13. In certain embodiments, the ELP contains repeat units, including tandem repeating units, of Val-Pro-Gly-X-Gly (SEQ ID NO: 3), where X is as defined above, and where the percentage of Val-Pro-Gly-X-Gly units taken with respect to the entire ELP component (which may comprise structural units other than VPGXG) is greater than about 50%, or greater than about 75%, or greater than about 85%, or greater than about 95% of the ELP. The ELP may contain motifs of 5 to 15 structural units (e.g. about 10 structural units) of SEQ ID NO: 3, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V, G, and A. In some embodiments, the ELP includes the ELP 1 series (VPGXG: V5A2G3). In some embodiments, the ELP includes the amino acid sequence of SEQ ID NO: 21. In some embodiments, the ELP includes the ELP 4 series (VPGXG: V-5). In some embodiments, the ELP includes a combination of the ELP1 and ELP4 series. Without being bound by theory, the differences in the ELP polymer hydrophobicity is determined by the guest residues and their ratios, with the ELP 4 series being more hydrophobic than the ELP1 series.

In certain embodiments, the ELP is the ELP-1 series which includes [VPGXG]$_m$, where m is any number from 1 to 200, each X is selected from V, G, and A, and wherein the ratio of V:G:A may be about 5:3:2. In certain embodiments, ELP includes [VPGXG]$_{90}$, where each X is selected from V, G, and A, and wherein the ratio of V:G:A may be about 5:3:2. In certain embodiments, the ELP includes [VPGXG]$_{120}$, where each X is selected from V, G, and A, and wherein the ratio of V:G:A may be about 5:3:2.

In certain embodiments, the ELP includes [VPGXG]$_{144}$, where each X is selected from V, G, and A, and wherein the ratio of V:G:A is about 7.2:0. In certain embodiments, the ELP includes [VPGXG]$_1$, where each X is selected from V, G. and A, and wherein the ratio of VGA is about 70:2. In certain embodiments, the ELP includes [VPGXG]$_{144}$, where each X is selected from V, G, and A, and wherein the ratio of V:G:A is about 6:0-3. In certain embodiments, the ELP includes [VPGXG]$_1$, where each X is selected from V, G, and A, and wherein the ratio of V:G:A is about 5:2:2.

In certain embodiments, the ELP includes [XPGVG]$_m$, where m is any number from 1 to 200, each X is selected from V, G, and A. In certain embodiments, the ELP includes [XPGVG]$_{144}$, where m is any number from 1 to 200, each X is selected from V, G, and A and wherein the ratio of V:G:A is about 5:0:4. In certain embodiments, the ELP includes [XPGVG]$_{144}$, where each X is selected from V. G, and A, and wherein the ratio of V:G:A is about 5:0:4.

Alternatively, the ELP is the ELP-4 series which includes [VPGVG]$_{90}$, or [VPGVG]$_{120}$. One hundred and twenty structural units of this ELP can provide a transition temperature at about 37° C. with about 0.005 to about 0.05 mg/ml (e.g., about 0.01 mg/ml) of protein. Alternatively, the ELP includes [VPGXG]$_{144}$ or [XPGVG]$_{144}$. For example, 144 structural units of either of these ELPs can provide a transition temperature at between about 28° C. and 35° C.

In certain embodiments, the ELP contains repeat units, including tandem repeating units, of Xaa-Pro-Gly-Val-Gly (SEQ ID NO: 13), where X is as defined above, and where the percentage of Xaa-Pro-Gly-Val-Gly units taken with respect to the entire ELP component (which may include structural units other than XPGVG) is greater than about 50%, or greater than about 75%, or greater than about 85%, or greater than about 95% of the ELP. The ELP may contain motifs of 5 to 15 structural units (e.g. about 9 structural units) of SEQ ID NO: 13, with the guest residue X varying among at least 2 or at least 3 of the units in the motif. The guest residues may be independently selected, such as from non-polar or hydrophobic residues, such as the amino acids V, I, L, A, G, and W (and may be selected so as to retain a desired inverse phase transition property). In certain embodiments, the guest residues are selected from V and A.

In certain embodiments, the ELP contains repeat units, including tandem repeating units of any of SEQ ID NOs: 1-13 either alone or in combination. In one embodiment, the ELP contains repeats of two or more of any of SEQ ID NOs: 1-13 in combination. In certain embodiments, the ELP contains repeats of SEQ ID NO: 3 and SEQ ID NO: 13. In some embodiments, the ELP contains repeats of SEQ ID NO: 3 and SEQ ID NO: 13, wherein the guest residues are independently selected, such as from non-polar or hydrophobic residues, such as the amino acids V, I, L, A, G, and W (and may be selected so as to retain a desired inverse phase transition property). In certain embodiments, the guest residues are selected from V and A In some embodiments, the ELP comprises 9 mers comprising five copies of a pentapeptide disclosed herein. In some embodiments, the ELP comprises 9 mers comprising SEQ ID NOs: 3 and 13 in any combination. In some embodiments, the ELP comprises a sequence alternating between SEQ ID NOs: 3 and 13. In some embodiments, the ELP includes 9 mers including nine copies of one or more ELP structural units disclosed herein. In some embodiments, the ELP includes 9 mers including nine copies of a pentapeptide disclosed herein. In some embodiments, the ELP includes 9 mers including SEQ ID NOs: 3 and 13 in any combination. In some embodiments, the ELP includes a sequence alternating between SEQ ID NOs: 3 and 13. ELPs of varying numbers of 9 mers can be combined to produce ELPs with, for instance, 18, 27, 36, 45, 54, 63, 72, 81, 90, 99, 108, 117, 126, 135, 144, 153, 162, 171, or 180 copies of the 9 mer. In some embodiments, the ELP includes the amino acid sequence of SEQ ID NO: 20.

In certain embodiments, the ELP includes 9 mers including SEQ ID NO: 3, wherein the guest residue is selected from V, G, and A. In certain embodiments, the ELP includes 9 mers including SEQ ID NO: 3, wherein V, G, and A are in the ratio of 7:2:0 (alpha). In certain embodiments, the ELP includes 9 mers including SEQ ID NO:3, wherein V, G, and A are in the ratio of 7:0:2 (beta v1). In certain embodiments, the ELP includes 9 mers including SEQ ID NO:3, wherein V, G, and A are in the ratio of 6:0:3 (beta v2). In certain embodiments, the ELP includes 9 mers including SEQ ID NO:3, wherein V, G, and A are in the ratio of 5:2:2 (gamma). In certain embodiments, the ELP includes 9 mers including SEQ ID NO: 13, wherein the guest residue is selected from V, G, and A. In certain embodiments, the ELP includes 9 mers including SEQ ID NO:13, wherein V, G, and A are in the ratio of 5:0:4 (delta).

In some embodiments, the ELP includes combinations of the alpha, beta v1, beta v2, and/or delta 9 mers. For example, the gamma ELP is constructed by alternating between an alpha 9 mer and a beta v1 9 mer for 16 copies until a 144 mer is constructed. In certain embodiments, the FLP includes combinations of alpha and beta v1 9 mers. In certain embodiments, the ELP includes combinations of alpha and beta v2 9 mers. In certain embodiments, the ELP includes combinations of alpha and delta 9 mers. In certain embodiments, the ELP includes combinations of beta v1 and beta v2 9 mers. In certain embodiments, the ELP includes combinations of beta v1 and delta 9 mers. In certain embodiments, the ELP includes combinations of beta v2 and delta 9 mers. In certain embodiments, the ELP includes combinations of alpha, beta v1, and beta v2 9 mers. In certain embodiments, the ELP includes combinations of alpha, beta v1, and delta 9 mers. In certain embodiments, the ELP includes combinations of alpha, beta v2, and delta 9 mers. For example, in particular arrangements, the ELPbeta v2 may include the following guest residues in structural units iterated in the following sequence: A-V-A-V-V-A-V-A-V. The iterated sequence may be repeated sequentially in the ELP about 10 times, about 15 times, about 16 times, about 20 times, about 25 times, about 30 times, or about 35 times or more. In some aspects, the ELP contains about 10 to about 20 iterated sequences. In other aspects, the ELP contains about 15 to 20 iterated sequences. In some aspects, the ELP contains about 16 iterated sequences.

In some embodiments, the ELP includes 10 mers including ten copies of one or more ELP structural units disclosed herein. In some embodiments, the ELP includes 10 mers including ten copies of a pentapeptide disclosed herein. In some embodiments, the ELP includes 10 mers including SEQ ID NOs: 3 and 13 in any combination. In some embodiments, the ELP includes a sequence alternating between SEQ ID NOs: 3 and 13. ELPs of varying numbers of 10 mers can be combined to produce ELPs with, for instance, 20, 30, 40, 60, 90, 100, 120, 150, 160, or 200 copies of the 10 mer.

In some embodiments, the ELP may form a β-turn structure. Exemplary peptide sequences suitable for creating a β-turn structure are described in International Patent Application PCT/US96/05186. For example, the fourth residue (X) in the sequence VPGXG, can be altered without eliminating the formation of a β-turn.

The structure of exemplary ELPs may be described using the notation ELPk [$X_iY_j$-n], where k designates a particular ELP repeat unit, the bracketed capital letters are single letter amino acid codes and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG, where X is valine, alanine, and glycine at a relative ratio of about 5:2:3; ELP [$K_1V_2F_{1-4}$] designates an ELP component containing 4 repeating units of the pentapeptide VPGXG, where X is lysine, valine, and phenylalanine at a relative ratio of about 1:2:1; ELP1 [$K_1V_7F_1$-9] designates a polypeptide containing 9 repeating units of the pentapeptide VPGXG, where X is lysine, valine, and phenylalanine at a relative ratio of about 1:7:1; ELP1 [V-5] designates a polypeptide containing 5 repeating units of the pentapeptide VPGXG, where X is valine; ELP1 [V-20] designates a polypeptide containing 20 repeating units of the pentapeptide VPGXG, where X is valine; ELP2 [5] designates a polypeptide containing 5 repeating units of the pentapeptide AVGVP (SEQ ID NO: 4); ELP3 [V-5] designates a polypeptide containing 5 repeating units of the pentapeptide IPGXG (SEQ ID NO: 5), where X is valine; ELP4 [V-5] designates a polypeptide containing 5 repeating units of the pentapeptide LPGXG (SEQ ID NO: 7), where X is valine.

With respect to the ELP, the Tt is a function of the hydrophobicity of the guest residue. Thus, by varying the identity of the guest residue(s) and their mole fraction(s), ELPs can be synthesized that exhibit an inverse transition over a broad range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from: glutamic acid, cysteine, lysine, aspartate, alanine, asparagine, serine, threonine, glycine, arginine, and glutamine.

For polypeptides having a molecular weight >100,000 Da, the hydrophobicity scale disclosed in PCT/US96/05186 provides one means for predicting the approximate Tt of a specific ELP sequence. For polypeptides having a molecular weight <100.000 Da, the Tt may be predicted or determined by the following quadratic function. Tt=M0+M1X+M2X2 where X is the MW of the fusion protein, and M0=116.21; M1=−1 7499; M2=0.010349.

The FLP in some embodiments is selected or designed to provide a Tt ranging from about 10 to about 37° C. at formulation conditions, such as from about 20 to about 37° C., or from about 25 to about 37° C. In some embodiments, the transition temperature at physiological conditions (e.g., 0.9% saline) is from about 34 to 36° C., to take into account a slightly lower peripheral temperature.

Elastin-like-peptide (ELP) protein polymers and recombinant fusion proteins can be prepared as described in U.S. Patent Publication No. 2010/0022455. In some embodiments, the ELPs are constructed through recursive ligation to rapidly clone highly repetitive polypeptides of any sequence and specified length over a large range of molecular weights. In a single cycle, two halves of a parent plasmid, each containing a copy of an oligomer, are ligated together, thereby dimerizing the oligomer and reconstituting a functional plasmid. This process is carried out recursively to assemble an oligomeric gene with the desired number of repeats. For example, one ELP structural subunit (e.g. a pentapeptide or a 9 mer of pentapeptides) is inserted into a vector. The vector is digested, and another ELP structural unit (e.g. a pentapeptide or a 9 mer of pentapeptides) is inserted. Each subsequent round of digestion and ligation doubles the number of ELP structural units contained in the resulting vector until the ELP polymer is the desired length.

In other embodiments, the ELP includes a random coil or non-globular extended structure. For example, the ELP includes an amino acid sequence disclosed in U.S. Patent Publication No. 2008/0286808, WIPO Patent Publication No. 2008/155134, and U.S. Patent Publication No. 2011/0123487.

For example, in some embodiments the ELP amino acid sequence includes an unstructured recombinant polymer of at least 40 amino acids. For example, the unstructured polymer may be defined where the sum of glycine (G), aspartate (D), alanine (A), serine (S), threonine (T), glutamate (E) and proline (P) residues contained in the unstructured polymer, constitutes more than about 80% of the total amino acids. In some embodiments, at least 50% of the amino acids are devoid of secondary structure as determined by the Chou-Fasman algorithm. The unstructured polymer includes more than about 100, 150, 200 or more contiguous amino acids. In some embodiments, the amino acid sequence forms a random coil domain. In particular, a polypeptide or amino acid polymer having or forming "random coil conformation" substantially lacks a defined secondary and tertiary structure.

In various embodiments, the intended subject is human, and the body temperature is about 37° C., and thus the therapeutic agent is designed to provide a sustained release at or near this temperature (e.g. between about 28° C. to about 37° C.). A slow release into the circulation with reversal of hydrogen bonding and/or hydrophobic interactions is driven by a drop in concentration as the product diffuses at the injection site, even though body temperature remains constant. In other embodiments, the subject is a non-human mammal, and the therapeutic agent is designed to exhibit a sustained release at the body temperature of the mammal, which may be from about 30 to about 40° C. in some embodiments, such as for certain domesticated pets (e.g., dog or cat) or livestock (e.g., cow, horse, sheep, or pig). Generally, the Tt is higher than the storage conditions of the formulation (which may be from about 2° C. to about 30° C., or about 10° C. to about 25° C., or from about 15° C. to about 22° C., or about 2° C. to about 8° C.), such that the therapeutic agent remains in solution for injection. Alternatively, the therapeutic agent may be stored frozen, such as from about −80° C. to about −20° C.

In some embodiments, the ELP can provide a transition temperature at a range of 27° C. to 36° C. inclusive. In some embodiments, the ELP can provide a transition temperature at a range of 28° C. to 35° C. inclusive. In some embodiments, the ELP can provide a transition temperature at a range of 29° C. to 34° C. inclusive. In some embodiments, the ELP can provide a transition temperature at a range of 27° C. to 33° C. inclusive. In some embodiments, the ELP can provide a transition temperature at a range of 30° C. to 33° C. inclusive. In some embodiments, the ELP can provide a transition temperature at a range of 31° C. to 31° C. inclusive. In some embodiments, the ELP can provide a transition temperature of 27° C., 28° C. 29° C., 30° C., 31° C., 32° C., 33° C., 34° C., 35° C., or 36° C. In some embodiments, the ELP can provide a transition temperature at a range of 28° C. to 35° C. inclusive at a protein concentration of 10 mg/mL in 110 mM NaCl.

In some embodiments, the ELP protein polymers are constructed through recursive ligation to rapidly clone DNA encoding highly repetitive polypeptides of any sequence and specified length over a large range of molecular weights. In a single cycle, two halves of a parent plasmid, each containing a copy of an oligomer, are ligated together, thereby dimerizing the oligomer and reconstituting a functional plasmid. This process is carried out recursively to assemble an oligomeric gene with the desired number of repeats. For example, one ELP structural subunit (e.g. a pentapeptide or a 9 mer of pentapeptides) is inserted into a vector. The vector is digested, and another ELP structural unit (e.g. a pentapeptide or a 9 mer of pentapeptides) is inserted. Each subsequent round of digestion and ligation doubles the number of ELP structural units contained in the resulting vector until the ELP polymer is the desired length. By varying the number of pentapeptides in the initial structural unit, ELPs of varying length can easily be constructed. Alternative means of construction (i.e. other than recursive ligation) can be used to produce alternative lengths of ELP.

In some embodiments, the vector contains one or more additional amino acids or ELP structural unit repeats. For example, the vector may add an additional pentamer repeat to the N terminus of the ELP with valine in the guest position and an additional pentamer to the C terminus with a tryptophan in the guest residue. The tryptophan may be used as a means to increase the extinction coefficient of the molecule, allowing for better measurement of absorbance, for instance at 280 nm, which can be useful for determination of protein concentration, or for monitoring protein content during purification. The pentamers added to either end can also be designed so as the encoding DNA contains restriction enzyme recognition sites for cloning of fusion partners on to either end of the ELP coding sequence.

In some embodiments, the therapeutic composition includes an active agent and one or more ELPs. In some embodiments, the therapeutic composition includes an active agent with one or more ELPs at either the N- or C-terminus. In some embodiments, the therapeutic composition includes an active agent with one or more ELPs at both the N- or C-termini. In some embodiments, the ELPs are approximately the same size. In some embodiments, the ELPs differ in size. In some embodiments, an ELP at one terminus is larger than an ELP at the other terminus. In some embodiments, an ELP at the N-terminus is larger than an ELP at the C-terminus. In some embodiments, an ELP at the C-terminus is larger than an ELP at the N-terminus.

Myopathies and Methods of Treatment

Myopathies are neuromuscular diseases in which the muscle fibers do not function for any one of many reasons, resulting in muscular weakness Phenotypically, these diseases are characterized by inflammation of the muscle tissue, skeletal-muscle wasting, muscle loss, and fibrosis which can cause premature death through respiratory and cardiac failure. Muscle myopathies may affect any type of muscle, including skeletal muscle, cardiac muscle, and/or smooth muscle. In some embodiments, the myopathy is characterized by increased muscle fibrosis. In some embodiments, the myopathy is characterized by decreased muscle strength and/or force contractility. In some embodiments, the myopathy is characterized by decreased myocyte shortening. In some embodiments, the myopathy is characterized by decreased myocyte re-lengthening velocity. In some embodiments, the myopathy is characterized by decreased myocyte relaxation. In some embodiments, the myocyte is a skeletal muscle myocyte. In some embodiments, the myocyte is a cardiomyocyte.

In some aspects, the present disclosure provides a method of treating muscle myopathy comprising administering pharmaceutical compositions of a vasoactive intestinal peptide and one or more ELPs to a subject in need. In some aspects, the present disclosure provides a method of preventing muscle myopathy comprising administering pharmaceutical compositions of a vasoactive intestinal peptide and one or more ELPs to a subject in need. In some aspects, the present disclosure provides a method of delaying muscle myopathy comprising administering pharmaceutical compositions of a vasoactive intestinal peptide and one or more ELPs to a subject in need. In some aspects, the present disclosure provides a method of slowing the progression of muscle myopathy comprising administering pharmaceutical compositions of a vasoactive intestinal peptide and one or more ELPs to a subject in need. In some aspects, the present disclosure provides a method of ameliorating muscle myopathy comprising administering pharmaceutical compositions of a vasoactive intestinal peptide and one or more ELPs to a subject in need.

Types of myopathies that may be treated, prevented, delayed, or ameliorated by the pharmaceutical compositions disclosed herein include, but are not limited to, muscular dystrophies, myotonia, neuromyotonia, congenital myopathies (e.g. nemaline myopathy. multi/minicore myopathy, centronuclear myopathy), mitochondrial myopathies, familial periodic paralysis, inflammatory myopathies, metabolic myopathies (e g. glycogen storage diseases, lipid storage disorder); acquired myopathies (e.g. drug-induced myopathy, glucocorticoid myopathy, alcoholic myopathy), dermatomyositis, polymyositis, inclusion body myositis, myositis ossificans, rhabdomyolysis and myoglobinurias.

Types of muscular dystrophy that may be treated, prevented, delayed, or ameliorated by the pharmaceutical compositions disclosed herein include, but are not limited to, BMD (Becker Muscular Dystrophy), DMD (Duchenne Muscular Dystrophy), Myotonic Dystrophy, LGMD (Limb Girdle Muscular Dystrophy), Oculopharyngeal Muscular Dystrophy, Congenital Muscular Dystrophy, Distal Muscular Dystrophy, Landouzy-Dejerine Muscular Dystrophy, Emery-Dreifuss muscular dystrophy, and Facioscapulohumeral Muscular Dystrophy.

Cardiomyopathy is the measurable deterioration of the myocardium's ability to contract, leading to heart failure. The disease progresses over time with variable onset of arrhythmias and ventricle dysfunction. Electrocardiographic abnormalities can be found early in the disease and progress with age. Development of cardiomyopathy is characterized by initial diastolic dysfunction followed by eccentric hypertrophy.

In some aspects, the present disclosure provides methods of treating cardiomyopathy comprising administering pharmaceutical compositions of a vasoactive intestinal peptide and one or more ELPs to a subject in need. In some aspects, the present disclosure provides a method of preventing cardiomyopathy comprising administering pharmaceutical compositions of a vasoactive intestinal peptide and one or more ELPs to a subject in need. In some aspects, the present disclosure provides a method of delaying cardiomyopathy comprising administering pharmaceutical compositions of a vasoactive intestinal peptide and one or more ELPs to a subject in need. In some aspects, the present disclosure provides a method of slowing the progression of cardiomyopathy comprising administering pharmaceutical compositions of a vasoactive intestinal peptide and one or more ELPs to a subject in need. In some aspects, the present disclosure provides a method of ameliorating cardiomyopathy comprising administering pharmaceutical compositions of a vasoactive intestinal peptide and one or more ELPs to a subject in need.

Types of cardiomyopathy that may be treated, prevented, delayed, or ameliorated by the pharmaceutical compositions disclosed herein include, but are not limited to, genetic cardiomyopathies (e.g. hypertrophic cardiomyopathy (HCM or HOCM); arrhythmogenic right ventricular cardiomyopathy (ARVC); isolated ventricular non-compaction, mitochondrial myopathy), dilated cardiomyopathy (DCM), restrictive cardiomyopathy (RCM), acquired cardiomyopathies (e.g. peripartum cardiomyopathy: Takotsubo cardiomyopathy; Loeffler endocarditis), metabolic/storage cardiomyopathies (e.g. amyloidosis, hemochromatosis), inflammatory cardiomyopathies (e.g. "viral myocarditis"; cardiomyopathy caused by Chagas disease), endocrine cardiomyopathies (e g. diabetic cardiomyopathy; cardiomyopathy caused by hyperthyroidism; acromegaly), cardiomyopathies caused by toxicity (e g. chemotherapy cardiomyopathy, alcoholic cardiomyopathy), X-linked dilated cardiomyopathy, and/or neuromuscular cardiomyopathies (e.g. muscular dystrophy) In some preferred embodiments, the cardiomyopathy results from a muscular dystrophy. In some embodiments, the cardiomyopathy results from Duchenne Muscular Dystrophy. In some embodiments, the cardiomyopathy results from Becker Muscular Dystrophy.

The treatment, prevention, delay, or amelioration of cardiomyopathic symptoms may be measured by any means known in the art. For example, evaluation may include echocardiographic evaluation, cardia magnetic resonance imagining (MRI), cardiac MRI with late gadolinium enhancement. In particular, the LV size, thickness, volumes, EF, and scar/inflammatory burden of the myocardium, as well as strain may be evaluated. Strain, change in LV dimension and volume, and scar burden are key measures.

The treatment, prevention, delay, or amelioration of myopathic symptoms may be measured by any means known in the art. For example, tests used to evaluate patients with myopathies include, but are not limited to, creatine kinase (CK) levels with isoenzymes, levels of electrolytes, calcium, and magnesium, serum myoglobin levels, serum creatinine and blood urea nitrogen levels, urinalysis (e.g. myoglobinuria indicated by positive urinalysis with few red blood cells on microscopic evaluation, complete blood count, erythrocyte sedimentation rate, thyroid function tests, aspartate aminotransferase levels, electrocardiography, antinuclear antibody levels, electromyography, magnetic resonance imaging, and/or muscle biopsy. The effects of administration of the pharmaceutical compositions disclosed herein may be measured in any relevant muscle, including but not limited to skeletal muscle, cardiac muscle, gastrocnemius muscle, quadriceps muscle, diaphragm muscle, and/or tibialis anterior muscle.

In some aspects, the present disclosure provides a method of preventing cardiac deterioration comprising administering pharmaceutical compositions of a vasoactive intestinal peptide and one or more ELPs to a subject in need. In some aspects, the present disclosure provides a method of delaying cardiac deterioration comprising administering pharmaceutical compositions of a vasoactive intestinal peptide and one or more ELPs to a subject in need. In some aspects, the present disclosure provides a method of slowing the progression of cardiac deterioration comprising administering pharmaceutical compositions of a vasoactive intestinal peptide and one or more ELPs to a subject in need. In some aspects, the present disclosure provides a method of ameliorating cardiac deterioration comprising administering pharmaceutical compositions of a vasoactive intestinal peptide and one or more ELPs to a subject in need. In some embodiments, cardiac deterioration is prevented, delayed, or ameliorated for about 1 week, about 1 month, about 2 months, about 3 months, about 4 months, about 5 months, about 6 months, about 8 months, about 1 year, about 2 years, about 5 years, and/or about 10 years compared with the cardiac deterioration in an untreated myopathic subject. In some embodiments, cardiac deterioration is prevented, delayed, or ameliorated by about 1%, about 5%, about 10%, about 20%, about 30%, about 40%, about 50%, about 60%, about 70%, about 80%, or about 90% compared with cardiac deterioration in an untreated myopathic subject. In some embodiments, this prevention, delay, or amelioration of cardiac deterioration is observed at the time points disclosed herein. For example, cardiac deterioration may be delayed by about 20% at 32 weeks. In some embodiments, the cardiac deterioration is a decrease in inotropy. In some embodiments, the cardiac deterioration is a decrease in lusitropy. In some embodiments, the cardiac deterioration is a thickening of the heart muscle. In some embodiments, the cardiac deterioration is cardiac hypertrophy.

In some embodiments, administration of the pharmaceutical compositions disclosed herein improve cardiac function in a subject compared to an untreated myopathic subject. In some embodiments, cardiac function is improved for about 1 week, about 1 month, about 2 months, about 3 months, about 4 months, about 5 months, about 6 months, about 8 months, about 1 year, about 2 years, about 5 years, and/or about 10 years compared with cardiac function of an untreated myopathic subject. In some embodiments, cardiac function is improved by about 1%. about 5%, about 10%, about 20%, about 30%, about 40%, about 50%, about 60%, about 70%, about 80%, or about 90% compared with cardiac function of an untreated myopathic subject. In some embodiments, this improvement in cardiac function is observed at the time points disclosed herein. In some embodiments, the cardiac improvement is an increase in inotropy. In some embodiments, the cardiac improvement is an increase in lusitropy. In some embodiments, the cardiac improvement is less thickening of the heart muscle compared to a cardiomyopathy subject. In some embodiments, the cardiac improvement is less cardiac hypertrophy compared to a cardiomyopathy subject.

In some aspects, the present disclosure provides a method of preventing the development of fibrosis comprising administering pharmaceutical compositions of a vasoactive intestinal peptide and one or more ELPs to a subject in need. In some aspects, the present disclosure provides a method of delaying the development of fibrosis comprising administering pharmaceutical compositions of a vasoactive intestinal peptide and one or more ELPs to a subject in need. In some aspects, the present disclosure provides a method of slowing the progression of fibrosis comprising administering pharmaceutical compositions of a vasoactive intestinal peptide and one or more ELPs to a subject in need. In some aspects, the present disclosure provides a method of ameliorating the development of fibrosis comprising administering pharmaceutical compositions of a vasoactive intestinal peptide and one or more ELPs to a subject in need. In some embodiments, development of fibrosis is prevented, delayed, or ameliorated for about 1 week, about 1 month, about 2 months, about 3 months, about 4 months, about 5 months, about 6 months, about 8 months, about 1 year, about 2 years, about 5 years, and/or about 10 years compared with the development of fibrosis in an untreated myopathic subject. In some embodiments, the development of fibrosis is prevented, delayed, or ameliorated by about 1%, about 5%, about 10%, about 20%, about 30%, about 40%, about 50%, about 60%, about 70%, about 80%, or about 90% compared with the development of fibrosis in an untreated myopathic subject. In some embodiments, this prevention, delay, or amelioration of fibrosis is observed at the time points disclosed herein. In some embodiments, fibrosis is measured using histological techniques on a biopsy (e.g. hematoxylin and eosin (HE) and trichrome staining) where fibrosis can be assessed by determining the percentage of collagen present versus the total tissue area.

In some aspects, the present disclosure provides a method of reducing the production of collagen comprising administering pharmaceutical compositions of a vasoactive intestinal peptide and one or more ELPs to a subject in need. In some aspects, the present disclosure provides a method of delaying the production of collagen comprising administering pharmaceutical compositions of a vasoactive intestinal peptide and one or more ELPs to a subject in need. In some aspects, the present disclosure provides a method of ameliorating the production of collagen comprising administering pharmaceutical compositions of a vasoactive intestinal peptide and one or more ELPs to a subject in need. In some embodiments, production of collagen is reduced, delayed, or ameliorated for about 1 week, about 1 month, about 2 months, about 3 months, about 4 months, about 5 months, about 6 months, about 8 months, about 1 year, about 2 years, about 5 years, or about 10 years compared with the production of collagen in an untreated myopathic subject. In some embodiments, the production of collagen is reduced, delayed, or ameliorated by about 1%, about 5%, about 10%, about 20%, about 30%, about 40%, about 50%, about 60%, about 70%, about 80%, or about 90% compared with the production of collagen in an untreated myopathic subject. In some embodiments, this reduction, delay, or amelioration of collagen production is observed at the time points disclosed herein. For example, the amount of collagen produced in a myopathic patient may be decreased by about 25% at 32 weeks.

In some embodiments, administration of the pharmaceutical compositions disclosed herein maintains muscle contractility and/or contractile force in a subject. In some embodiments, the muscle contractility and/or contractile force is maintained at about 20%, about 30%, about 40%, about 50%, about 60%, about 70%, about 80%, about 90%, about 95%, or about 99% of the muscle contractility and/or contractile force of a healthy subject. In some embodiments, administration of the pharmaceutical compositions disclosed herein maintains muscle contractility and/or contractile force in a subject for about 1 week, about 1 month, about 2 months, about 3 months, about 4 months, about 5 months, about 6 months, about 8 months, about 1 year, about 2 years, about 5 years, and/or about 10 years compared to the muscle contractility and/or contractile force of a healthy subject. In some embodiments, the degree of muscle contractility and/or contractile force is maintained in the subject at the time points disclosed herein. A healthy subject is defined as a subject who is not suffering from a muscular dystrophy or other muscle wasting disease or disorder.

In some embodiments, administration of the pharmaceutical compositions disclosed herein maintains muscle strength in a subject. In some embodiments, muscle strength is maintained at about 20%, about 30%, about 40%, about 50%, about 60%, about 70%, about 80%, about 90%, about 95%, or about 99% of the muscle strength of a healthy subject. In some embodiments, administration of the pharmaceutical compositions disclosed herein maintains muscle strength in a subject for about 1 week, about 1 month, about 2 months, about 3 months, about 4 months, about 5 months, about 6 months, about 8 months, about 1 year, about 2 years, about 5 years, and/or about 10 years compared to the muscle strength of a healthy subject. In some embodiments, the degree of muscle strength is maintained in the subject at the time points disclosed herein. Muscle function may be measured at the whole subject level, at the organ level, and/or the myocyte level. Skeletal muscle strength may be measured by any means known in the art, and for example, by manual muscle-testing and/or the use of a dynamometer. Cardiac muscle strength may be measured by any means known in the art, and for example, through the use of electrocardiograms, echocardiography, magnetic resonance imaging (MRI), pressure volume assessment (e.g. ejection fraction, fractional shortening, end diastolic volume (EDV), end systolic volume (ESV), stroke volume (SV), myocardial strain, end diastolic pressure (EDP), end systolic pressure (ESP)). For example, in some embodiments, administration of the pharmaceutical composition preserves fractional area shortening compared to an untreated myopathic subject. In some embodiments, administration of the pharmaceutical composition preserves ejection fraction compared to an untreated myopathic subject. In some embodiments, administration of the pharmaceutical composition increases the ventricular filling velocity compared to an untreated myopathic subject. In some embodiments, administration of the pharmaceutical composition elevates the maximal rate of pressure rise compared to an untreated myopathic subject. In still other embodiments, administration of the pharmaceutical composition increases the Tau constant of relaxation compared to an untreated myopathic subject.

In some embodiments, administration of the pharmaceutical compositions disclosed herein prevent, delay, or ameliorate contraction-induced muscle injury in a subject. In some embodiments, administration of the pharmaceutical compositions disclosed herein prevent, delay, or ameliorate contraction-induced muscle injury by about 20%, about 30%, about 40%, about 50%, about 60%, about 70%, about 80%, about 90%, and/or about 95% compared with an untreated myopathic subject. In some embodiments, administration of the pharmaceutical compositions disclosed herein prevents, delays, or ameliorates contraction-induced muscle injury in a subject for about 1 week, about 1 month, about 2 months, about 3 months, about 4 months, about 5 months, about 6 months, about 8 months, about 1 year, about 2 years, about 5 years, and/or about 10 years compared with an untreated myopathic subject. In some embodiments, the degree of prevention, delay, or amelioration of contraction-induced muscle injury is observed in the subject at the time points disclosed herein. For example, administration of the pharmaceutical compositions disclosed herein may reduce contraction-induced muscle injury by 25% at 10 weeks. In some embodiments, administration of the pharmaceutical compositions disclosed herein prevent, delay, or ameliorate contraction-induced muscle injury in a subject without changing specific muscle force. In some embodiments, administration of the pharmaceutical compositions disclosed herein prevent, delay, slow the progression, or ameliorate contraction-induced muscle injury in a subject and improve specific muscle force.

In some embodiments, administration of the pharmaceutical compositions disclosed herein maintains myocyte function. In some embodiments, administration of the pharmaceutical compositions disclosed herein maintain myocyte shortening, myocyte re-lengthening, relaxation, and/or myocyte contractility. In some embodiments, myocyte shortening, myocyte re-lengthening, relaxation, and/or myocyte contractility is maintained at about 20%, about 30%, about 40%, about 50%, about 60%, about 70%, about 80%, about 90%, about 95%, and/or about 99% of the myocyte shortening, myocyte re-lengthening, relaxation, and/or myocyte contractility in a healthy subject. In some embodiments, administration of the pharmaceutical compositions disclosed herein maintains myocyte shortening, myocyte re-lengthening, relaxation, and/or myocyte contractility in a subject for about 1 week. about 1 month, about 2 months, about 3 months, about 4 months. about 5 months, about 6 months. about 8 months, about 1 year, about 2 years, about 5 years, and/or about 10 years compared with myocyte shortening, myocyte re-lengthening, relaxation, and/or myocyte contractility in a healthy subject. In some embodiments, the maintenance of the degree of myocyte shortening, myocyte re-lengthening, relaxation, and/or myocyte contractility is observed in the subject at the time points disclosed herein. Myocyte function can be assayed through any means known in the art, including for example, the measurement of biomarkers associated with function and/or damage, and/or direct testing of the myocytes. In some embodiments, the myocytes are skeletal myocytes. In some embodiments, the myocytes are cardiomyocytes.

In some embodiments, administration of the pharmaceutical compositions disclosed herein affects the immune cell count in a muscle. In some embodiments, administration of the pharmaceutical compositions disclosed herein decreases the immune cell count in a muscle. In some embodiments, administration of the pharmaceutical compositions disclosed herein decreases macrophage count in a muscle. In some embodiments, the immune cell count is decreased by about 10%, about 20%, about 30%, about 40%, about 50%, about 60%, about 70%, about 80%, about 90%, about 95% or about 99% of the immune cell count in the muscle of an untreated myopathic subject. In some embodiments, administration of the pharmaceutical compositions disclosed herein decreases the immune cells count in the muscle of a subject for about 1 week, about 1 month, about 2 months, about 3 months, about 4 months, about 5 months, about 6 months, about 8 months, about 1 year, about 2 years, about 5 years, and/or about 10 years compared with the immune cell count in the muscle of an untreated myopathic subject. In some embodiments, this decrease in immune cell count in a muscle is observed in the subject at the time points disclosed herein. For example, administration of the pharmaceutical compositions disclosed herein may decrease the immune cell count in a muscle by about 25% at 32 weeks.

In some aspects, the present disclosure provides a method of preventing inflammation comprising administering pharmaceutical compositions of a vasoactive intestinal peptide and one or more ELPs to a subject in need. In some aspects, the present disclosure provides a method of delaying inflammation comprising administering pharmaceutical compositions of a vasoactive intestinal peptide and one or more ELPs to a subject in need. In some aspects, the present disclosure provides a method of slowing the development of inflammation comprising administering pharmaceutical compositions of a vasoactive intestinal peptide and one or more ELPs to a subject in need. In some aspects, the present disclosure provides a method of ameliorating inflammation comprising administering pharmaceutical compositions of a vasoactive intestinal peptide and one or more ELPs to a subject in need. In some aspects, the present disclosure provides a method of reducing inflammation comprising administering pharmaceutical compositions of a vasoactive intestinal peptide and one or more ELPs to a subject in need. In some embodiments, inflammation is prevented, delayed, reduced, or ameliorated for about 1 week, about 1 month, about 2 months, about 3 months, about 4 months, about 5 months, about 6 months, about 8 months, about 1 year, about 2 years, about 5 years, and/or about 10 years compared with the inflammation in an untreated myopathic subject. In some embodiments, inflammation is prevented, delayed, reduced, or ameliorated by about 1%, about 5%, about 10%, about 20%, about 30%, about 40%, about 50%, about 60%, about 70%, about 80%, or about 90% compared with inflammation in an untreated myopathic subject. In some embodiments, this prevention, delay, reduction, or amelioration of inflammation is observed at the time points disclosed herein. In some embodiments, administration of the pharmaceutical compositions disclosed herein prevents, delays, reduces, or ameliorates inflammation by inhibiting pro-inflammatory cytokine expression or activity. In some embodiments, the pro-inflammatory cytokine is any pro-inflammatory cytokine, including but not limited to, OPN, LTβ4, TNF-alpha, interleukin-6 (IL-6) and soluble tumor necrosis factor-alpha receptor (sTNFR).

Pharmaceutical Compostions and Administration

The present disclosure provides pharmaceutical compositions including a Vasoactive Intestinal Peptide and one or more ELPs with one or more pharmaceutically acceptable excipients and/or diluents.

The present disclosure provides sustained release formulations including a therapeutic agent disclosed herein and one or more pharmaceutically acceptable excipients and/or diluents. For example, such excipients include salts, and other excipients that may act to stabilize hydrogen bonding Any appropriate excipient known in the art may be used. Exemplary excipients include, but are not limited to, amino acids such as histidine, glycine, or arginine; glycerol; sugars, such as sucrose; surface active agents such as polysorbate 20 and polysorbate 80, citric acid; sodium citrate; antioxidants; salts including alkaline earth metal salts such as sodium, potassium, and calcium; counter ions such as chloride and phosphate; preservatives; sugar alcohols (e.g. mannitol, sorbitol); and buffering agents. Exemplary salts include sodium chloride, potassium chloride, magnesium chloride, calcium chloride, sodium phosphate dibasic. sodium phosphate monobasic, potassium phosphate monobasic, and potassium phosphate dibasic. In certain embodiments, the pharmaceutical compositions disclosed herein have enhanced efficacy. bioavailability, therapeutic half-life, persistence, degradation resistance, etc.

In certain embodiments, the formulation may include from about 5 mM histidine to about 100 mM histidine. In some embodiments, the formulation includes about 50 mM histidine, about 40 mM histidine, about 30 mM histidine, about 25 mM histidine, about 20 mM histidine, or about 15 mM histidine. In certain embodiments, the formulation may include from about 10 mM sodium chloride to about 200 mM sodium chloride. In some embodiments, the formulation includes about 20 mM sodium chloride, about 40 mM sodium chloride, about 60 mM sodium chloride, about 75 mM sodium chloride, about 100 mM sodium chloride, about 120 mM sodium chloride, or about 150 mM sodium chloride. In certain embodiments, the formulation may include from about 10 mM histidine to about 30 mM histidine and from about 60 mM sodium chloride to about 80 mM sodium chloride. In certain embodiments, the formulation may include about 20 mM histidine and about 75 mM sodium chloride.

The pharmaceutical composition is formulated at a pH, ionic strength, and generally with excipients sufficient to enable the formation of the matrix at body temperature (e.g., 37° C., or at from 34 to 36° C. in some embodiments). The pharmaceutical composition is generally prepared such that it does not form the matrix at storage conditions. The formulation can be stored frozen, refrigerated or at room temperature. The storage condition may be below freezing, such as lower than about −10° C., or lower than about −20° C., or lower than about −40° C., or lower than about −70° C. Storage conditions are generally less than the transition temperature of the formulation, such as less than about 32° C., or less than about 30° C., or less than about 27° C., or less than about 25° C., or less than about 20° C., or less than about 15° C. In some embodiments, the formulation is stored at 2°-8° C. For example, the formulation may be isotonic with blood or have an ionic strength that mimics physiological conditions. For example, the formulation may have an ionic strength of at least that of 25 mM Sodium Chloride, or at least that of 30 mM Sodium chloride, or at least that of 40 mM Sodium Chloride, or at least that of 50 mM Sodium Chloride, or at least that of 75 mM Sodium Chloride, or at least that of 100 mM Sodium Chloride, or at least that of 150 mM Sodium Chloride. In certain embodiments, the formulation has an ionic strength equivalent to that of 0.9% saline (154 mM sodium chloride).

In some embodiments, the formulation is formulated at physiological pH. In some embodiments, the formulation is formulated at a pH in the range of about 5.5 to about 8.5. In some embodiments, the formulation is formulated at a pH in the range of about 6.0 to about 8.0. In some embodiments, the formulation is formulated at a pH in the range of about 6.5 to about 7.5. In some embodiments, the formulation is formulated at a pH of 7.5. In some embodiments, formulations with a lower pH demonstrate improved formulation stability compared to formulations at a higher pH. In some embodiments, formulations with a higher pH demonstrate improved formulation stability compared to formulations at a lower pH.

In some embodiments, the formulation is stable at storage conditions. Stability can be measured using any appropriate means in the art. Generally, a stable formulation is one that shows less than a 5% increase in degradation products or impurities. In some embodiments, the formulation is stable for at least about 1 month, at least about 2 months, at least about 3 months, at least about 4 months, at least about 5 months, at least about 6 months, at least about one year, or at least about 2 years or more at the storage conditions. In some embodiments, the formulation is stable for at least about 1 month, at least about 2 months, at least about 3 months. at least about 4 months, at least about 5 months, at least about 6 months, or at least about one year or more at 25° C.

The protein concentration in the formulation is tailored to enable the formation of the coacervate at the temperature of administration. For example, higher protein concentrations help drive the formation of the coacervate, and the protein concentration needed for this purpose varies depending on the ELP series used. For example, in some embodiments using an ELP1-120, or ELPs with comparable transition temperatures, the protein is present in the range of about 1 mg/mL to about 200 mg/mL, or is present in the range of about 5 mg/mL to about 125 mg/mL. In embodiments using an ELP4-120, or amino acid sequences with comparable transition temperatures, the protein is present in the range of about 0.005 mg/mL to about 10 mg/mL, or is present in the range of about 0.01 mg/mL to about 5 mg/mL.

In exemplary embodiments, the disclosure provides a sustained release pharmaceutical composition that includes a vasoactive intestinal peptide disclosed herein (e.g. having an N-terminal moiety such as a Methionine) and one or more amino acid sequences including $[VPGXG]_{90}$, $[VPGXG]_{120}$, $[VPGXG]_{160}$, or $[VPGXG]_{180}$, where each X is selected from V, G, and A. V, G, and A may be present at a ratio of about 5:3:2, of about 7:2:0, of about 7:0:2, of about 6:0:3, or of about 5:2:2. Alternatively, the amino acid sequence includes $[VPGVG]_{90}$ or $[VPGVG]_{120}$. In exemplary embodiments, the disclosure provides a sustained release pharmaceutical composition that includes a vasoactive intestinal peptide or derivatives thereof (e.g. having an N-terminal moiety such as a Methionine) and one or more amino acid sequences including $[XPGVG]_{144}$, where each X is selected from V, G, and A. V, G, and A may be present at a ratio of about 5:0:4. Alternatively, the amino acid sequence includes [XPGVG]$_{144}$. The formulation further includes one or more pharmaceutically acceptable excipients and/or diluents for formation of a reversible matrix from an aqueous form upon administration to a human subject. VIP and derivatives thereof are disclosed in U.S. Patent Publication No. 2011/0178017.

In another aspect, the disclosure provides a method for delivering a sustained release regimen of a vasoactive intestinal peptide disclosed herein. The method comprises administering the pharmaceutical composition described herein to a subject in need, wherein the pharmaceutical composition is administered from about to about 8 times per month. In some embodiments, the pharmaceutical composition is administered about 1 time, about 2 times, about 3 times, and/or about 4 times per month. In some embodiments, the pharmaceutical composition is administered weekly. In some embodiments, the pharmaceutical composition is administered daily. In some embodiments, the pharmaceutical composition is administered from one to three times weekly. In some embodiments, the pharmaceutical composition is administered once every two weeks. In some embodiments, the pharmaceutical composition is administered from one to two times a month. In particular embodiments, the pharmaceutical composition is administered about 1 time per month. In some embodiments, the pharmaceutical composition is administered about once every 2 months, about once every 3 months, about once every 4 months, about once every 5 months, and/or about once every 6 months. In some embodiments, VIP may have an additional moiety such as Methionine at the N-terminus to alter the receptor binding profile, as described in U.S. Patent Publication No. 2011/0178017. In some embodiments, VIP is fused to ELP1 (having from about 90 to about 180 ELP units) In some embodiments, VIP is fused to ELP4 (having from about (having from about 90 to about 180 ELP units). In some embodiments, VIP is fused to ELPbeta v2 (having from about 90 to about 180 ELP units). The pharmaceutical composition can be packaged in the form of pre-filled pens or syringes for administration once per week, twice per week, or from one to eight times per month, or alternatively filled in conventional vials and the like.

Advantageously, the compositions provide for prolonged pharmacokinetic exposure due to sustained release of the active agent. In particular aspects, the maximal exposure level may be achieved at about 10 hours, about 24 hours, about 48 hours or about 72 hours after administration; typically the maximum exposure level is achieved between about 10 hours and about 48 hours after administration. After the maximal exposure level is achieved the compositions may achieve a sustained level of release whereby a substantial percentage of the maximal level is obtained for a period of time. For example, the sustained level may about 50%, about 60%, about 70%, about 80%, about 90% or about 100%. Exemplary periods of time for maintaining the sustained rate are about 3 days, about 4 days, about 5 days, about 6 days, about 1 week, about 2 weeks, about 4 weeks, about 6 weeks, or about 8 weeks, after the maximal exposure rate is achieved. Subsequently, the sustained level may lower to a reduced exposure level Such reduced exposure rates may be about 5%, about 10%, about 20%, about 30%, about 40%, about 50% or about 60%.

In some embodiments. the pharmaceutical compositions disclosed herein are administered chronically. In some embodiments, the pharmaceutical compositions disclosed herein are administered for about 6 months, for about 7 months, for about 8 months, for about 9 months, for about 10 months, for about 11 months, for about 1 year, for about 2 years, for about 3 years, for about 4 years, for about 5 years, for about 10 years or more. The pharmaceutical compositions may be administered at any required dose and/or frequency disclosed herein.

In some embodiments, the pharmaceutical compositions disclosed herein are administered until myopathic symptoms improve. In some embodiments, the pharmaceutical compositions disclosed herein are administered until myopathic symptoms are ameliorated. In some embodiments, the pharmaceutical compositions disclosed herein are administered until myopathic symptoms are delayed. In some embodiments, the pharmaceutical compositions disclosed herein are administered until myopathic symptoms are cured.

In some embodiments, the pharmaceutical compositions disclosed herein are administered before the patient begins to exhibit one or more myopathic symptoms. In some embodiments, the pharmaceutical compositions disclosed herein are administered at the onset of myopathic symptoms. In some embodiments, the pharmaceutical compositions disclosed herein are administered before the patient begins to exhibit cardiomyopathy. In some embodiments, the pharmaceutical compositions disclosed herein are administered at the onset of cardiomyopathy symptoms.

In some embodiments, the pharmaceutical composition is administered to a subject determined to have muscle wasting. In some embodiments, the pharmaceutical composition is administered to a subject determined to have muscle myopathy. In some embodiments, the subject is determined to have increased levels of muscle protein circulating in the blood compared to a non-myopathic subject. In some embodiments, the subject is determined to have increased levels of creatine kinase (CK) circulating in the blood compared to a non-myopathic subject. In some embodiments, the subject is determined to have increased levels of lactic dehydrogenase (LDH) circulating in the blood compared to a non-myopathic subject. In some embodiments, the subject is determined to have increased levels of pyruvate kinase (PK) circulating in the blood compared to a non-myopathic subject. Muscle protein levels can be determined using a serum enzyme test.

In some embodiments, the subject is determined to have altered levels of electrolytes in the urine. In some embodiments, the subject is determined to have increased levels of calcium in the urine compared to non-myopathic subjects. In some embodiments, the subject is determined to have increased levels of magnesium in the urine compared to non-myopathic subjects Urine electrolyte levels can be determined using a urine test.

In some embodiments, the pharmaceutical composition is administered to a subject determined to have an inflammatory myopathy. In some embodiments, the subject is determined to have increased levels of antibodies circulating in the blood compared to a non-myopathic subject. In some embodiments, the subject is determined to have increased levels of myositis-associated antibodies circulating in the blood compared to a non-myopathic subject. In some embodiments, the myositis-associated antibodies include, but not limited to, Jo-1, PL-7, P-12, EK, OJ, KS, Zo and Ha. In some embodiments, the myositis-associated antibodies bind to antigens including, but not limited to, those bound by the antibodies Jo-1, PL-7, PI-12, EK, OJ, KS, Zo and Ha. In some embodiments, the antibodies include, but are not limited to, SRP, Mi-2, PMS1, P155, p140, CADM-140, MJ (p140), MU, SAE, decorin, KU, KJ, HMGCR, Mup44, Cortactin, nuclear pore, FHL1, PM-Scl, 56 kD, SSA/ro, U1-nRNP, U2-NRNP, Fer, MAS, and mitochondrial. In some embodiments, the antibodies bind to antigens including, but not limited to, those bound by the SRP, Mi-2, PMS1, P155, p140, CADM-140, MJ (p140), MU, SAE, decorin, KU, KJ, HMGCR, Mup44, Cortactin, nuclear pore, FHL1, PM-Scl, 56 kD, SSA/ro, U1-nRNP, U2-NRNP, Fer, MAS, and mitochondrial antibodies.

In some embodiments, the subject is determined to have abnormal echocardiograms compared to a non-cardiomyopathic subject. In some embodiments, the subject is determined to have changes in cardiac performance compared to a non-cardiomyopathic subject. In some embodiments, the subject is determined to have an increased P—R interval compared to non-cardiomyopathic subjects. In some embodiments, the subject is determined to have increased U waves compared to non-cardiomyopathic subjects. In some embodiments, the subject is determined to have wide QRS compared to non-cardiomyopathic subjects. In some embodiments, the subject is determined to have nonspecific ST-T changes compared to non-cardiomyopathic subjects. In some embodiments, the subject is determined to have sinus arrhythmias compared to non-cardiomyopathic subjects. In some embodiments, the subject is determined to have deep Q waves and elevated R waves precordially compared to non-cardiomyopathic subjects. In some embodiments, the subject is determined to have an abnormal tonic contraction (TC) compared to non-cardiomyopathic subjects. In some embodiments, tonic contraction results from a period of calcium dysregulation which manifests as sustained ion-driven myocyte contraction, resulting in echocardiographic appearance of left ventricle "underfilling" (Su et al (2015). In some embodiments, the subject is determined to have an arrhythmia compared to non-cardiomyopathic subjects. In some embodiments, the subject is determined to have an sinus tachycardia compared to non-cardiomyopathic subjects. In some embodiments, the subject is determined to have systolic dysfunction compared to non-cardiomyopathic subjects. In some embodiments, the subject is determined to have diastolic dysfunction compared to non-cardiomyopathic subjects. In some embodiments, the subject is determined to have decreased mitral systolic wave velocity compared to non-cardiomyopathic subjects. In some embodiments, the subject is determined to have wall motion abnormalities compared to non-cardiomyopathic subjects. The heart function and/or characteristics may be measured using electrocardiogram.

In some embodiments, the subject is determined to have increased pro-inflammatory cytokine expression compared to a non-cardiomyopathic subject. In some embodiments, the subject is determined to have increased pro-inflammatory cytokine activity compared to a non-cardiomyopathic subject. In some embodiments, the pro-inflammatory cytokine is any pro-inflammatory cytokine, including but not limited to, OPN, LTβ4, TNF-alpha, interleukin-6 (IL-6) and soluble tumor necrosis factor-alpha receptor (sTNFR). The expression or activity of pro-inflammatory cytokines in a subject may be measured through cytokine assays.

In some embodiments, the subject is determined to have decreased nNOS protein expression compared to a non-cardiomyopathic subject. In some embodiments, the subject is determined to have decreased nNOS activity compared to a non-cardiomyopathic subject. In some embodiments, the subject is determined to have altered nNOS protein accumulation compared to a non-cardiomyopathic subject. In some embodiments, the subject is determined to have increased nNOS protein accumulation in the cytosol of skeletal muscle compared to a non-cardiomyopathic subject.

In some embodiments, the subject is determined to have decreased nNOS protein accumulation in the sarcolemma of skeletal muscle compared to a non-cardiomyopathic subject Protein accumulation may be assayed through histological techniques. Protein expression may be assayed through immunoprecipitation techniques Protein activity may be measured by NOS catalytic assays.

The pharmaceutical composition is generally for "systemic delivery," meaning that the agent is not delivered locally to a pathological site or a site of action Instead, the agent is absorbed into the bloodstream from the injection site, where the agent acts systemically or is transported to a site of action via the circulation. The therapeutic agent may be administered by any known route, such as for example, orally, intravenously, intramuscularly, nasally, subcutaneously, intra-vaginally, and intra-rectally. In one embodiment, the formulation is generally for subcutaneous administration. In one embodiment, the pharmacokinetic (PK) parameters are prolonged when the agent is administered subcutaneously. In one embodiment, the half-life of the fusion protein is prolonged. In one embodiment, the PK parameters when the agent is administered subcutaneously are prolonged compared with the agent administered by other means (e.g. intravenously). In one embodiment, the depot of the agent is prolonged when the agent is administered subcutaneously compared with the agent administered by other means (e.g. intravenously).

In some embodiments, the formulation is administered about monthly, and may be administered subcutaneously or intramuscularly. In some embodiments, the formulation is administered about weekly, and may be administered subcutaneously or intramuscularly. In some embodiments, the site of administration is not a pathological site, for example, is not the intended site of action.

In various embodiments, the plasma concentration of the active agent does not change by more than a factor of 10, or a factor of about 5, or a factor of about 3 over the course of a plurality of administrations, such as at least 2, at least about 5, or at least about 10 administrations of the formulation. The administrations are substantially evenly spaced, such as, for example, about daily, or about once per week, or from one to about five times per month, or about once every two months, or about once every three months.

The pharmaceutical compositions disclosed herein may be administered in smaller doses and/or less frequently than unfused or unconjugated counterparts. While one of skill in the art can determine the desirable dose in each case, a suitable dose of the therapeutic agent for achievement of therapeutic benefit, may, for example, be in a range of about 1 microgram (μg) to about 100 milligrams (mg) per kilogram body weight of the recipient per day, preferably in a range of about 10 μg to about 50 mg per kilogram body weight per day and most preferably in a range of about 100 μg to about 10 mg per kilogram body weight per day. In some embodiments, the pharmaceutical composition is administered at a low dose. In some embodiments, the pharmaceutical composition is administered at a dose between 1 mg per kilogram per body weight per day to about 9 mg per kilogram per body weight per day. In some embodiments, the pharmaceutical composition is administered at about 1 mg per kilogram body weight per day, about 3 mg per kilogram body weight per day, and/or about 9 mg per kilogram body weight per day. The desired dose may be presented as one dose or two or more sub-doses administered at appropriate intervals throughout the day. These sub-doses can be administered in unit dosage forms, for example, containing from about 10 g to about 1000 mg, preferably from about 50 μg to about 500 mg, and most preferably from about 50 μg to about 250 mg of active ingredient per unit dosage form. Alternatively, if the condition of the recipient so requires, the doses may be administered as a continuous infusion.

In certain embodiments, the subject is a human, but in other embodiments may be a non-human mammal, such as a domesticated pet (e.g., dog or cat), or livestock or farm animal (e.g., horse, cow, sheep, or pig).

Combination Therapies

The pharmaceutical compositions disclosed herein may be administered with various therapies used to treat, prevent, delay, or ameliorate myopathies, muscular dystrophies, and/or cardiomyopathies, including, but not limited to, physical therapy, respiratory therapy, speech therapy, occupational therapy, corrective surgery, and/or therapeutic agents. The pharmaceutical compositions disclosed herein may be used alone or in combination with one or more therapeutic agents. The one or more therapeutic agents may be any compound, molecule, or substance that exerts therapeutic effect to a subject in need thereof.

The one or more therapeutic agents may be "co-administered", i.e., administered together in a coordinated fashion to a subject, either as separate pharmaceutical compositions or admixed in a single pharmaceutical composition. By "co-administered", the one or more therapeutic agents may also be administered simultaneously with the present pharmaceutical compositions, or be administered separately, including at different times and with different frequencies. The one or more therapeutic agents may be administered by any known route, such as orally, intravenously, intramuscularly, nasally, subcutaneously, intra-vaginally, intra-rectally, and the like; and the therapeutic agent may also be administered by any conventional route. In many embodiments, at least one therapeutic agent may be administered subcutaneously.

These one or more therapeutic agents include, but are not limited to, corticosteriods; steroids, phenytoin, procainamide; quinine; glucorticoids (e.g. deflazacort, VBP15, prednisone triamcinolone, methylprednisolone systemic, betamethasone, budesonide, prednisolone, hydrocortisone, dexamethasone, and/or cortisone); anticonvulsants; immunosuppressants (e.g. cyclosporine, tacrolimus, prednisolone, hydrocortisone, sirolimus, everolimus, azathioprine, mycophenolic acid, methotrexate, basiliximab, daclizumab, rituximab, anti-thymocyte globulin, anti-lymphocyte globulin); penicillins (e.g. penicillin and amoxicillin); cephalosporins (e.g. cephalexin); macrolides (e.g. erythromycin, clarithromycin, and azithromycin); fluoroquinolones (e.g. ofloxacin, levofloxacin, and ofloxacin); sulfonamides (e.g. co-trimoxazole and trimethoprim); tetracyclines (e.g. tetracycline and doxycycline); aminoglycosides (e.g. gentamicin and tobramycin)); ACE inhibitors (e.g. perindopril and enalapril); angiotensin II receptor blockers; beta blockers; calcium channel blockers; digoxin; antiarrhythmics; anticoagulants; antibiotics; diuretics (e.g. spironolactone, eplerenone); exon-skipping therapies (e.g. eteplirsen, drisapersen); anti-myostatin antibodies (e.g. PF-06252616); anti-connective tissue growth factor antibodies (e.g. FG-3019), PDE5 inhibitors (e.g. tadalafil, sildenafil); PDE9 inhibitors, NF-κB inhibitors, stop codon read-through drugs (e.g. ataluren); utrophin modulators (e.g. SMT C1100, SMT022357), antifibrotic agents (e.g. halofuginone. angiotensin [1-7]); synthetic analogs of coenzyme $Q_{10}$ (e.g. idebenone); allogeneic cardiac cell therapy (e g. CAP-1002; Toll-like receptor antagonists (e.g. IMO-8400); mineralocorticoid-receptor antagonists; β-adrenoceptor antagonists; reservatol; SIRT1 activators.

When two or more therapeutic agents are used in combination, the dosage of each therapeutic agent is commonly identical to the dosage of the agent when used independently. However, when a therapeutic agent interferes with the metabolism of others, the dosage of each therapeutic agent is properly adjusted. Alternatively, where the two or more therapeutic agents show synergistic effects, the dose of one or more may be reduced. Each therapeutic agent may be administered simultaneously or separately in an appropriate time interval.

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

The term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

This disclosure is further illustrated by the following non-limiting examples.

EXAMPLES

Example 1—PB1046 Effects on Cardiomyopathy and Skeletal Muscle Myopathy in Muscular Dystrophy Patients A clinical trial is performed in Duchenne Muscular Dystrophy and Becker Muscular Dystrophy patients to test the efficacy of PB1046 treatment on delaying the onset of skeletal and cardiac symptoms.

Design: This is a randomized (2:1), double blind, placebo controlled trial. Initially patients 18 years old or older will be evaluated, but the study will open to adolescents 12 years old and older. In order to evaluate dose response, at least two dose levels will be evaluated, e.g. doses between 0.4 mg/kg and 3.2 mg/kg, for instance 0.8 mg/kg and 1.6 mg/kg. Depending on safety considerations, higher or lower doses may also be evaluated. At least six patients will be treated at each dose level.

The primary study endpoints are efficacy, which is measured as a change from baseline in global cardiac/regional function properties following 12 weeks of treatment. This function will additionally be evaluated at 24 weeks. Echocardiography and cardiac MRI with late gadolinium enhancement will be used for evaluation. The effect of treatment on left ventricular circumferential strain will be measured. Left ventricle end diastolic volume (LVEDV), right ventricle end diastolic volume (RVEDV), the degree of enhancement as a measurement of cardiac fibrosis, fractional shortening (FS), and/or cardiac output (CO) will be measured. LV size, thickness, volumes, ejection fraction, and scar/inflammatory burden of the myocardium, as well as strain, change in LV dimension and volume, and scar burden are key measures, The secondary efficacy endpoints are respiratory function, quantitative muscle strength, functional and quality assessments.

Once the study is over, patients will be offered continued open label therapy based on the recommendations of the Data Safety Monitoring Board.

Example 2—Chronic Treatment with PB1046, a Stable and Long-Acting Vasoactive Intestinal Peptide Receptor Agonist, Improves Cardiac and Skeletal Muscle Function in Mouse Models of Duchenne Muscular Dystrophy Materials and Methods: MDX (C57BL10/ScSnDMDmdx, dystrophin deficient, n=21) and DKO (double knockout) mdx/utrn−/− (dystrophin/utrophin deficient, n=13) mice were administered with PB1046 (1.5 mg/kg) or 0.9% NaCl saline (control) subcutaneously three times a week for the duration of the study (32 weeks for IDX and up to 4 weeks for DKO). Left ventricular function (via echocardiography; ECHO) and electrocardiography (ECG) changes were monitored during routine check-ups. Terminal assessments included either an anesthetized preparation in an instrumented animal with a pressure catheter to measure systemic/left ventricular hemodynamics or skeletal muscle strength evaluation on the extensor digitorium longus (EDL) (MDX only). Tissue samples were flash frozen or fixed in formalin for histological assessments (Sirius Staining and Macrophage and CD counting).

The most commonly used echocardiographic parameter of ventricular performance is fractional shortening (FS %) which is used as an estimate of myocardial contractility and is the ratio between the diameter of the left ventricle and the end of diastole and its diameter at the end of systole. Fractional Area shortening (FAS) and Fractional Shortening measured. To calculate FAS, left ventricular areas were visualized in short axis at the level of the papillary and using the cross-sectional images, end-diastolic and end-systolic endocardial borders were manually traced. FAS was determined in the animals before and during the course of treatment. The rate of left ventricle (LV) pressure rise in early systole ($dP/dt_{max}$) measures LV global contractility. The greater the contractile force exerted, the greater the rate of increase in left ventricular pressure. This rate can be measured invasively, for example, using high-fidelity micromanometer catheters inside the LV, as well as non-invasively, from a continuous wave Doppler examination of mitral regurgitation jet. Tau, which represents the exponential decay of the ventricular pressure during isovolumic relaxation was also measured. A longer Tau indicates heart dysfunction.

Extensor digitorum longus (EDL) muscles from both mouse legs were dissected at the tendons and placed in Krebs-Henselet (K-H) buffer. Muscles were analyzed as disclosed in Heller et al. (2013) and Rodino-Klapac et al. (2007) with some adaptations. Briefly, one tendon was tied to the lever arm of the force transducer and the other tendon was tied to a linear servomotor. Once the muscle was stabilized, it was set to an optimal length of 1 gram and subjected to a warm-up consisting of three 1 Hz twitches every 30 seconds followed by three 150 Hz twitches every minute. After a 3 minute rest period, the EDL was stimulated at 50, 100, 150, and 200 Hz, with a 1 minute rest period between each stimulus to determine the maximum tetanic force. Muscle length was measured following stimulation. Following a 5 minute rest, the susceptibility of the EDL muscle to contraction-induced damage was assessed. After 500 ms of stimulation, the muscle was lengthened by 10% of the optimal length and stimulated at 150 Hz for 700 ms. After the stimulation, the muscle was returned to the optimal length. The cycle was repeated every minute for a total of 10 cycles.

Specific force was calculated by dividing the maximum tetanic force by the EDL muscle cross-sectional area. For comparative purposes, all force measurements were expressed per unit cross-sectional area of the contractile material (CSA) (normalized isometric force or tension, $mN/mm^2$). CSA was calculated using the following equation:

$$CSA = \frac{\text{(muscle mass in g)}}{[\text{(optimal fiber length in cm)} \times \text{(muscle density in g/cm}^3)]}$$

In addition, tissue samples were analyzed by staining with Sirius Red to determine the extent of collagen deposition as a marker of fibrosis.

Figure 1B:
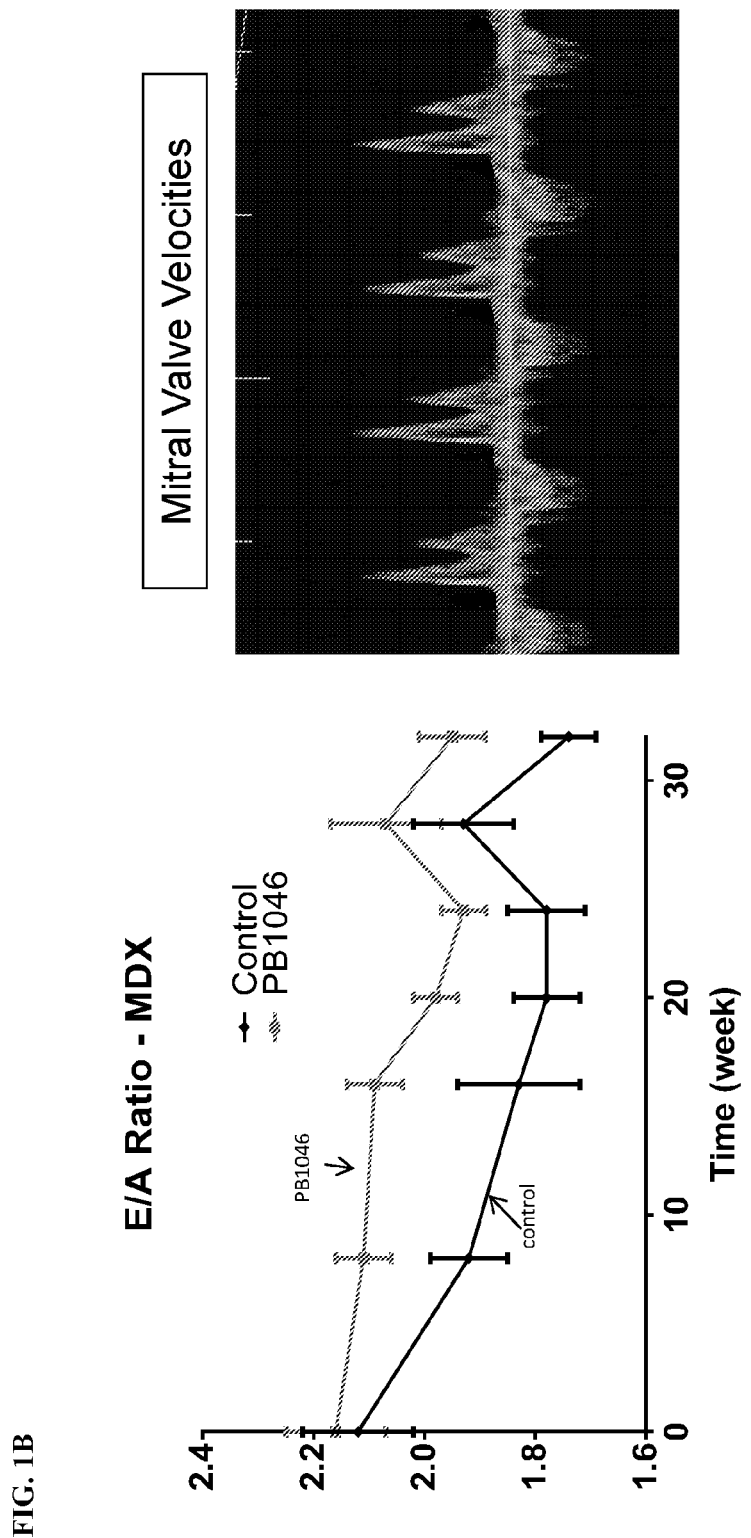

Results:

Chronic PB1046 slowed cardiac deterioration in MDX mice. The fractional area shortening (an index of systolic function) was preserved over the duration of the study ($P<0.05$) (FIG. 1A). Ventricular filling velocities (EA ratio—an index of diastolic function) tended to be faster throughout the study, but did not reach statistical significance (FIG. 1B). Fractional shortening (FS) was also preserved over the duration of the study (data not shown).

Electrocardiograms were also assessed at these time points. Throughout the study, PB1046 treated MDX mice tended to have shorter QRS (preserved ventricular conduction) when compared to placebo-treated animals, but did not reach statistical significance (data not shown). Similar trends were noted in DKO mice, with PB1046 treatment blunting the QRS prolongation noted in controls (data not shown).

Figure 2A:
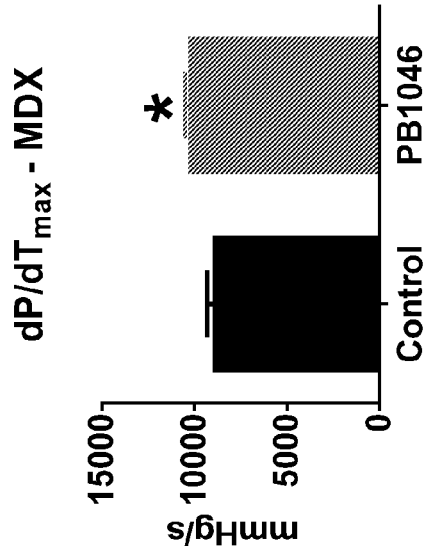
FIG. 2A-E shows the in vivo assessment of left ventricular function in MDX mice in a terminal procedure. n=4-5 (MDX) and n=2 (DKO), *P<0.05 vs controls. Both mdx and double knockout treated animals showed preserved $dP/dt_{max}$ (contraction) and faster Tau (relaxation).
Figure 2B:
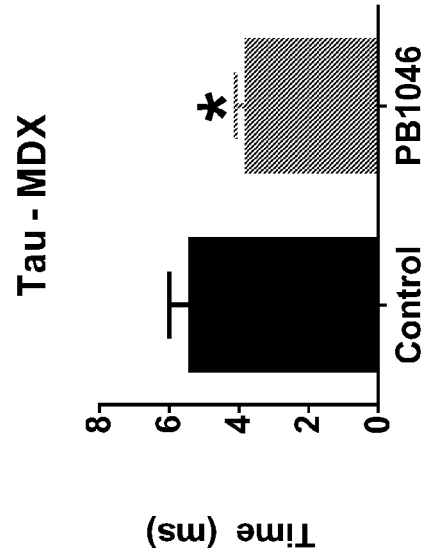
Figure 2C:
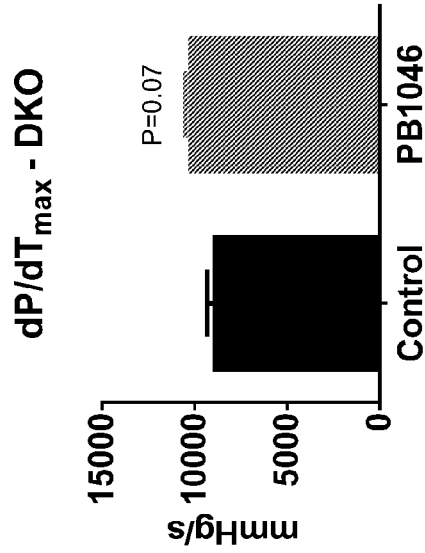
Figure 2D:
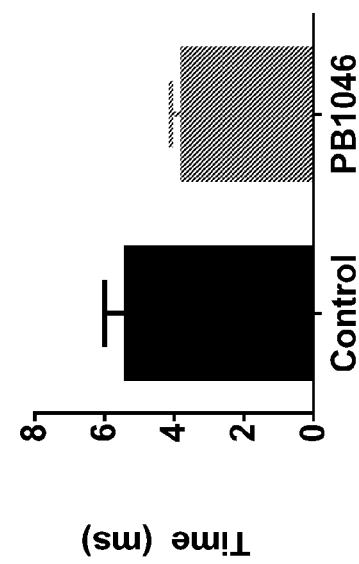
Figure 2E:
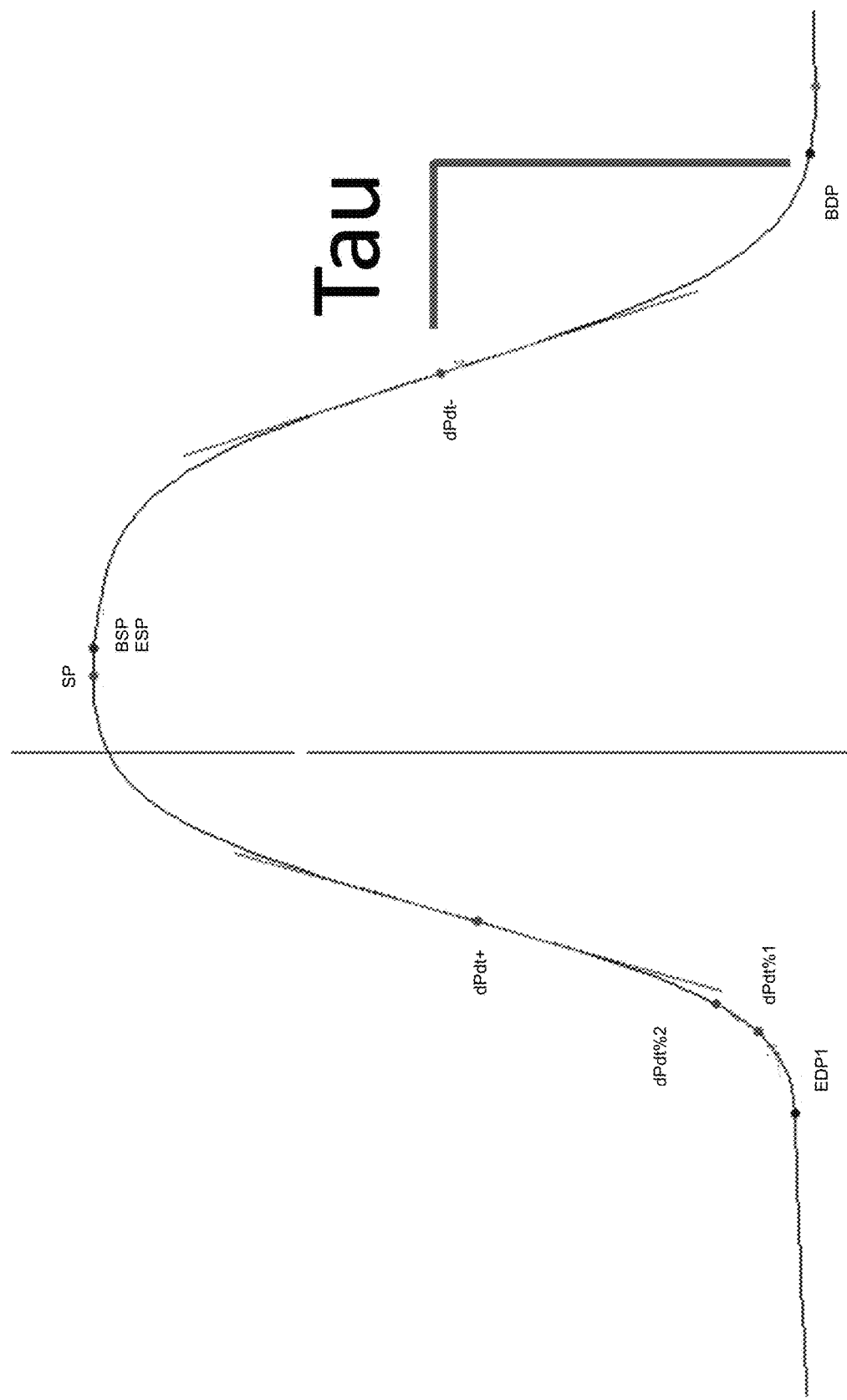

In vivo analysis showed that the elevated maximal rate of pressure rise ($dP/dt_{max}$—an index of systolic function) was significantly greater (FIG. 2A-B) and the Tau constant of relaxation was faster with PB1046 treatment in MDX mice ($P<0.05$) (FIG. 2C-E).

Figure 3A:
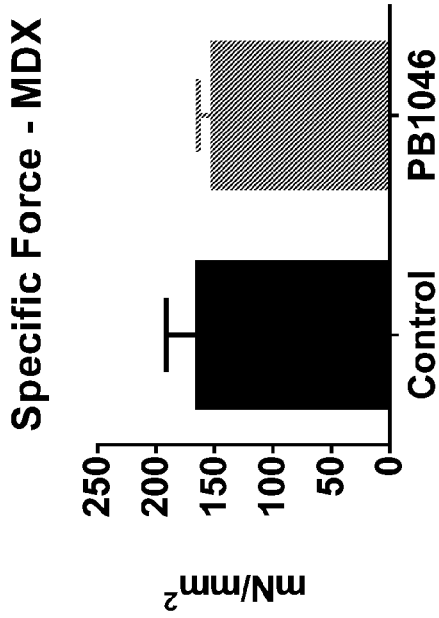
FIG. 3A-B shows the results from evaluation of skeletal muscle physiology in isolated extensor digitorum longus muscles from MDX mice. n=4-16. Treatment with PB1046 maintained eccentric contraction compared with untreated mice, indicating that the muscles in the treatment group were more resistant to contraction-induced damage.
Figure 3B:
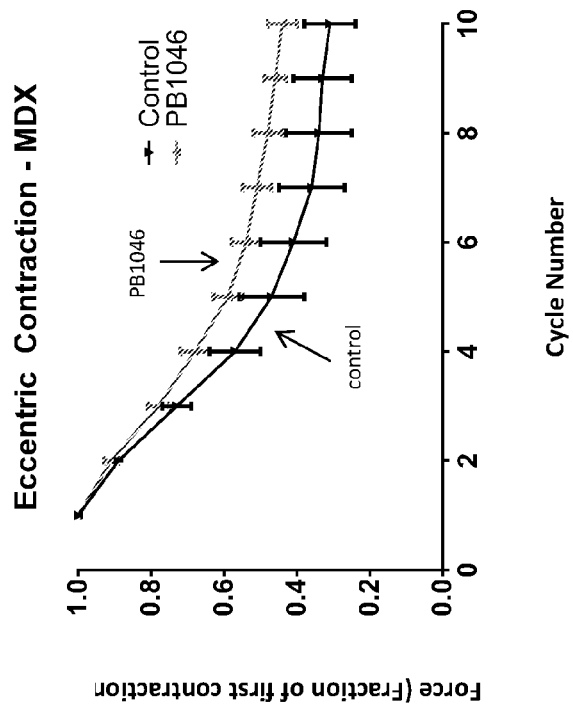

In evaluation of skeletal muscle function, PB1046 treatment protected against contraction-induced damage on isolated EDL muscles without changing specific force in MDX mice (FIG. 3A-B).

Figure 4A:
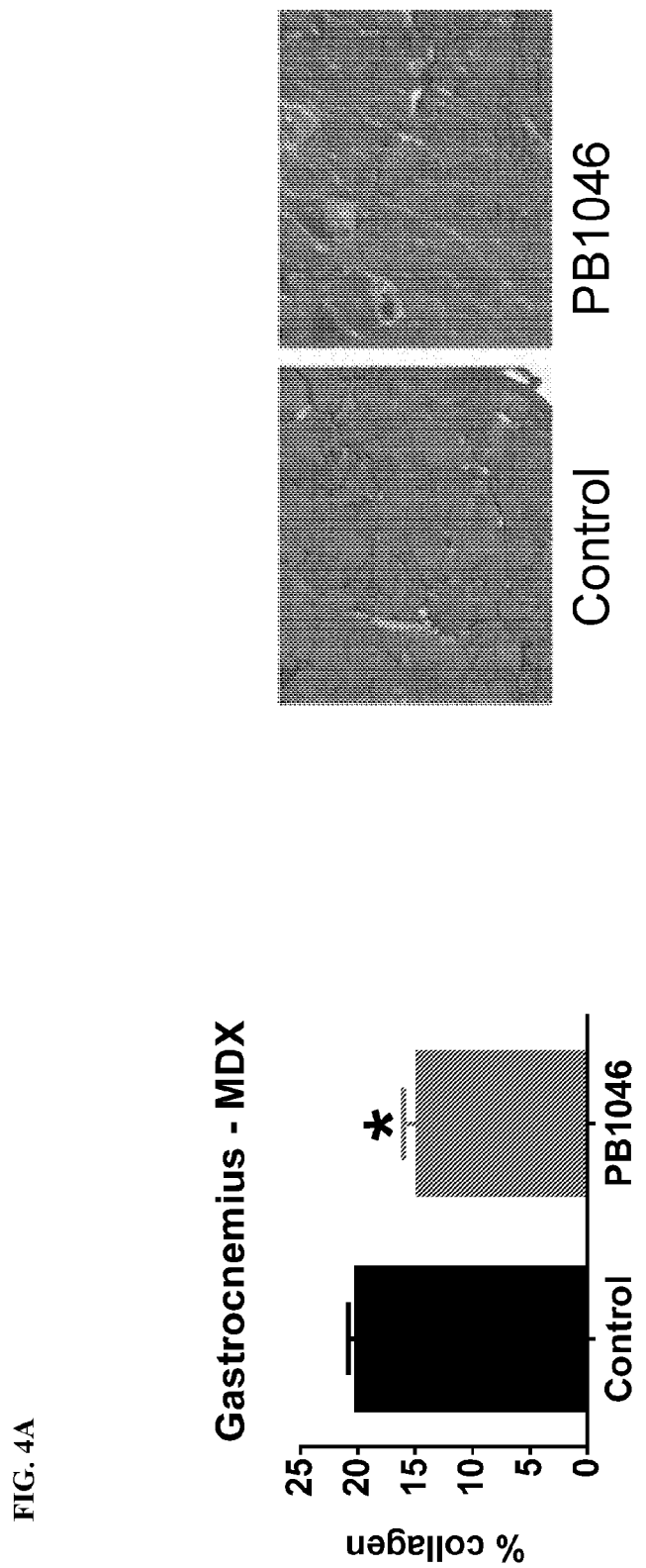
FIG. 4A-C shows collagen content (Panels A-B) in MDX mice measured with Sirius Red staining. Macrophage identification (Panel C) was determined via immunohistochemistry n=4-7, *P<0.05 vs controls. The degree of fibrosis as determined by collagen deposition was reduced in both skeletal muscle (gastrocnemius) and cardiac muscle.
Figure 4B:
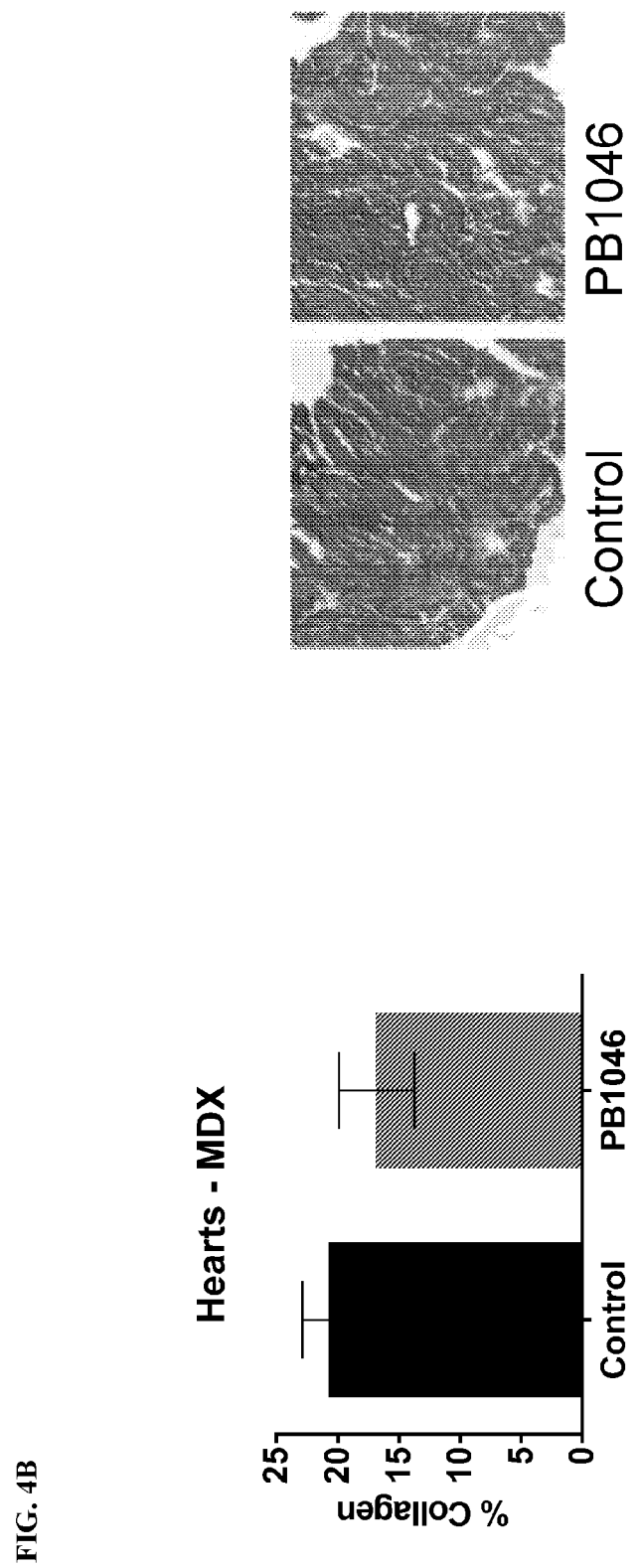

In agreement with increased skeletal and cardiac function, PB1046 significantly decreased the extent of fibrosis (collagen content) in the gastrocnemius muscle in the MDX mice (no statistically significant effect in quadriceps, diaphragm or tibialis anterior muscles, though trends were evident) (FIG. 4A). Additionally there was a trend to reduce collagen content in MDX heart muscle (FIG. 4B). Although n was small, similar trends in fibrosis were noted in DKO mice hearts (data not shown).

Figure 4C:
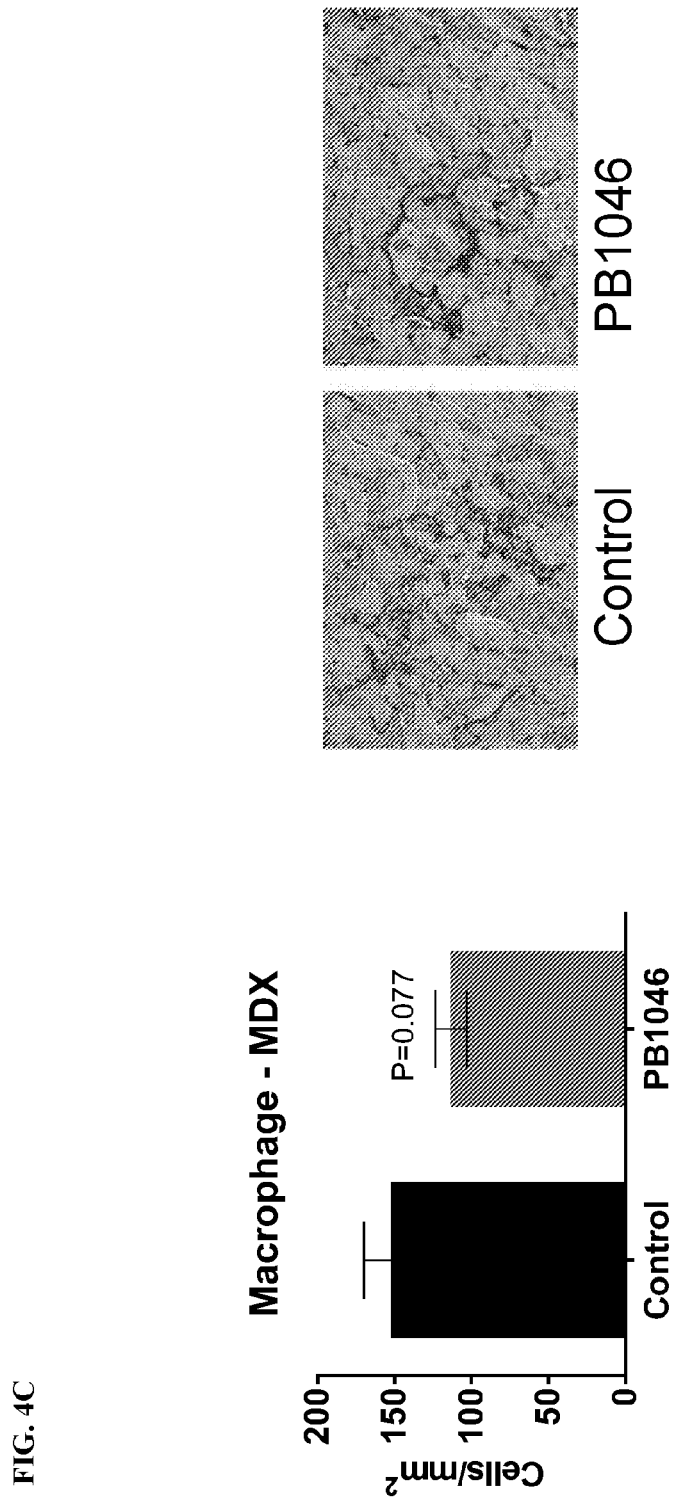

A significant reduction in total macrophage count was observed after treatment with PB1046 (FIG. 4C). While no differences were observed in other immune cells (CD3, CD4, CD8; data not shown).

Conclusion:

Chronic treatment with a novel VIP receptor agonist, PB1046, ameliorated DMD myopathy by slowing cardiac deterioration and protected against skeletal muscle contraction-induced damage. In addition to positive inotropic and lusitropic effects on cardiac function, decreased fibrosis (collagen content) is likely to contribute to positive effects of PB1046 on both cardiac and skeletal muscle.

INCORPORATION BY REFERENCE

All publications, patents, and patent publications cited are incorporated by reference herein in their entirety for all purposes.

This application incorporates by reference the following publications in their entireties for all purposes: US 2001/0034050; US 2009/0220455; U.S. Pat. No. 8,334,257; US 2013/0310538; US 2013/0172274; US 2011/0236384; U.S. Pat. Nos. 6,582,926, 7,429,458, 7,364,859; 8,178,495; US 2013/0079277; US 2013/0085099, US 2013/0143802; US 2014/0024600; US 2011/0178017; U.S. Pat. No. 7,709,227; US 2011/0123487, U.S. Pat. No. 8,729,018; US 20140171370, US 2013/0150291; WO/2014/113434: US 2014/0213516; and U.S. Application No. 62/082,945 filed Nov. 21, 2014.

REFERENCES

Ameen V. and Robson L G., Experimental models of Duchenne muscular dystrophy: relationship with cardiovascular disease. The Open Cardiovascular Medicine Journal, 2010; 4:265-277.

Barp A. et al. Genetic modifiers of Duchenne Muscular Dystrophy and dilated cardiomyopathy. PloS ONE. 2015. 10(10):e0141240. Doi: 10.1371/journalpone.014240.

Brenman J. et al. Nitric Oxide Synthase complexed with Dystrophin and absent from skeletal muscle sarcolemma in Duchenne Muscular Dystrophy. Cell. 1995. 82:743-752.

Bujak M. and Frangogiannis N G., The role of TGF-ß signaling in myocardial infarction and cardiac remodeling, 2007; 74(2):184-195.

Burks T N. and Cohn R D., Role of TGF-ß signaling in inherited and acquired myopathies, Skeletal Muscle, 2011; 1(19):1-13.

Bushby, K., et al., Diagnosis and management of Duchenne muscular dystrophy, part 1: diagnosis, and pharmacological and psychosocial management. The Lancet Neurology, 2010. 9(1): p. 77-93.

Byers, T J., L. M. Kunkel, and S. C. Watkins, The subcellular distribution of dystrophin in mouse skeletal, cardiac, and smooth muscle. The Journal of Cell Biology, 1991. 115(2): p. 411-421.

Chorny, A., et al., Signaling mechanisms of vasoactive intestinal peptide in inflammatory conditions. Regulatory Peptides, 2006. 137(1-2): p. 67-74.

Finsterer J, Cripe L., Treatment of dystrophin cardiomyopathies. Nature Reviews, 2014 (11): 168-178.

Heller, K N, Montgomery, C L, Janssen, P M, Clark, K R, Mendell, J R, and Rodino-Klapac, L R (2013). AAV-mediated overexpression of human alpha7 integrin leads to histological and functional improvement in dystrophic mice. Molecular therapy: the journal of the American Society of Gene Therapy 21: 520-525.

Henning, R. J. and D. R. Sawmiller, Vasoactive intestinal peptide: cardiovascular effects. Cardiovascular Research, 2001.49(1): p. 27-37.

Heydemann, A. and E. McNally, NO more muscle fatigue. The Journal of Clinical Investigation, 2009. 119(3): p. 448-450.

Hinkle et al. Activation of the vasoactive intestinal peptide 2 receptor modulates normal and atrophying skeletal muscle mass and force. Journal of Applied Physiology, 2005. 98(2):655-662.

Judge, D., et al., Pathophysiology and Therapy of Cardiac Dysfunction in Duchenne Muscular Dystrophy. American Journal of Cardiovascular Drugs, 2011. 11(5): p. 287-294.

Klingler, W., et al., The role of fibrosis in Duchenne muscular dystrophy. Acta Myologia, 2012 31(3): p. 184-219.

Lapidos, K. A., R Kakkar, and E. M. McNally, The Dystrophin Glycoprotein Complex: Signaling Strength and Integrity for the Sarcolemma. Circulation Research, 2004. 94(8): p. 1023-1031.

Politano, L. and G. Nigro. Treatment of dystophinopathic cardiomyopathy: a review of the literature and personal results. Acta Myologica. 2012. May 31(1): 24-30.

Rodino-Klapac, L R, et al. (2007). A translational approach for limb vascular delivery of the micro-dystrophin gene without high volume or high pressure for treatment of Duchenne muscular dystrophy. *Journal of translational medicine* 5: 45

Rosenberg A S et al. Immune-mediated pathology in Duchenne muscular dystrophy. Science Transl Med. 2015. 7(299): 299rv4. doi: 10.1126/scitranslmed.aaa7322.

Schellenberger, V. et al. A recombinant polypeptide extends the in vivo half-life of peptides and proteins in a tunable manner. Nat. Biotechnol. 2009 December; 27(12): 1186-90.

Schlapschy, M. et al. PASylation: a biological alternative to PEGylation for extending the plasma half-life of pharmaceutically active proteins. Protein Engineering, Design and Selection. 2013. 26 (8): 489-501.

Su, J A et al. (2015) Left Ventricular Tonic Contraction as a Novel Biomarker of Cardiomyopathy in Duchenne Muscular Dystrophy. Pediatr. Cardiol. December 29 [Epub ahead of print].

Sun, W., et al., Vasoactive intestinal peptide (VIP) inhibits TGF-β1 production in murine macrophages. Journal of neuroimmunology, 2000. 107(1): p. 88-99.

Townsend, D., et al., Distinct pathophysiological mechanisms of cardiomyopathy in hearts lacking dystrophin or the sarcoglycan complex. The FASEB Journal, 2011. 25(9): p. 3106-3114.

Villalta, S. A., et al., Regulatory T cells suppress muscle inflammation and injury in muscular dystrophy. Science Translational Medicine, 2014. 6(258): p. 258ra142.

Ye, V. Z. and K. A. Duggan, Vasoactive intestinal peptide down-regulates the intrahepatic renin-angiotensin system in the anaesthetized rat. Clin. Sci., 2000. 99(3):p. 201-206.

Zhou, L. and H. Lu, Targeting Fibrosis in Duchenne Muscular Dystrophy. Journal of Neuropathology & Experimental Neurology. 2010. 69(8): p. 771-776 10.1097/NEN.0b013e3181e9a34b.

The invention claimed is:

1. A method for slowing skeletal muscle deterioration in a patient having muscular dystrophy comprising administering to a patient in need thereof a pharmaceutical composition comprising a VPAC2-selective Vasoactive Intestinal Peptide (VIP) and an elastin-like peptide comprising at least 90 repeating units of VPGXG (SEQ ID NO: 3), where X is independently selected from Val, Ala, and Gly at a ratio of about 5:3:2.

2. The method of claim 1, wherein administration of the pharmaceutical composition reduces muscle fibrosis, preserves muscle contractility, or preserves muscle strength in the patient.

3. The method of claim 1, wherein administration of the pharmaceutical composition protects against muscle contraction-induced injury in the patient.

4. The method of claim 1, wherein the muscle myopathy is skeletal muscle myopathy.

5. The method of claim 1, wherein the pharmaceutical composition is formulated for subcutaneous, intramuscular, or intravenous administration.

6. The method of claim 1, wherein the pharmaceutical composition is administered at a low dose.

7. The method of claim 1, wherein the pharmaceutical composition is administered at a dose between 1 mg/kg per day and 10 mg/kg per day.

8. The method of claim 1, wherein the pharmaceutical composition is administered daily, from one to three times weekly, weekly, or from one to two times a month.

9. The method of claim 1, wherein administration of the pharmaceutical formulation preserves:
a) myocyte shortening compared to that of an untreated myocyte;
b) myocyte contractility compared to that of an untreated myocyte;
c) myocyte re-lengthening velocity compared to that of an untreated myocyte; or
d) myocyte relaxation compared to that of an untreated myocyte.

10. The method of claim 9, wherein the myocyte is a skeletal muscle myocyte.

11. The method of claim 1, wherein the skeletal muscular dystrophy is selected from the group consisting of Myotonic muscular dystrophy, Duchenne muscular dystrophy, Becker muscular dystrophy, Limb-girdle muscular dystrophy, Facioscapulohumeral muscular dystrophy, Congenital muscular dystrophy, Oculopharyngeal muscular dystrophy, Distal muscular dystrophy, and Emery-Dreifuss muscular dystrophy.

12. The method of claim 11, wherein the muscular dystrophy is Duchenne Muscular Dystrophy or Becker Muscular Dystrophy.

13. The method of claim 1, wherein the pharmaceutical composition comprises SEQ ID NO: 15.

14. The method of claim 1, wherein administration of the pharmaceutical composition:
a) decreases the collagen content in a muscle compared to an untreated myopathic patient; or
b) decreases immune cell count in muscle compared to an untreated myopathic patient.

15. The method of claim 14, wherein the immune cells is a macrophage.

* * * * *